United States Patent [19]

Heinz et al.

[11] Patent Number: 5,576,323
[45] Date of Patent: Nov. 19, 1996

[54] EXCITATORY AMINO ACID RECEPTOR ANTAGONISTS

[75] Inventors: Lawrence J. Heinz, Pittsboro; William H. W. Lunn; Darryle D. Schoepp, both of Indianapolis, all of Ind.

[73] Assignee: Eli Lilly and Company, Indianapolis, Ind.

[21] Appl. No.: 322,632

[22] Filed: Oct. 13, 1994

Related U.S. Application Data

[63] Continuation-in-part of Ser. No. 161,830, Dec. 3, 1993, abandoned.

[51] Int. Cl.$^6$ .................. A61K 31/435; A61K 31/41; A61K 31/34; A61K 31/195
[52] U.S. Cl. .................. 514/277; 514/345; 514/351; 514/359; 514/381; 514/384; 514/461; 514/473; 514/561; 514/562
[58] Field of Search .................. 514/468, 469, 514/443, 277, 360, 231.2, 361, 375, 384, 256, 453, 533, 561, 562, 345, 351, 359, 381, 461, 473

[56] References Cited

U.S. PATENT DOCUMENTS 4,428,960  1/1984  Heck.

FOREIGN PATENT DOCUMENTS 0348872  11/1988  European Pat. Off. .
0406863  1/1991  European Pat. Off. .

OTHER PUBLICATIONS

Evans, et al, Br. J. Pharmac. (1979), 67, 591–603.
Chemical Abstracts, 100, 22279h, 16 Jan. 1984.
Chemical Abstracts, 96, 163139y, 10 May 1982.
Chemical Abstracts, 75, 59821v, 30 Aug. 1971.
Tetrahedron Letters, vol. 30, No. 29, pp. 3799–3802, 1989, Miwa Yanagida et al., 'Synthesis of acyclic analogues of kainoids and neuroexcitatory activity'.
Tetrahedron Letters, vol. 31, No. 2, pp. 283–284, 1990. Michael R. Attwood et al., 'A new synthetic equivalent of the glutamic acid γ anion and its application to the synthesis of S–(+)–γ–carboxyglutamic acid'.
J. Org. Chem., 1991, 56,5729–5733, Isabelle Jako et al, 'Stereoselective synthesis of 3–alkylated glutamic acids: application to the synthesis of secokainic acid'.
Ohta, Hosoi, and Nozoe, "Stereoselective Hydroxylation of N–Carbamoyl–L–Pyroglutamate. Synthesis of (–)–Bulgecinine", Tet. Lett., 29, 329–332 (1988).
Chang, et al., "Study of the stereoselectivity of L–glutamate receptors by synthetic 4(R)–and 4(S)–substituted L–glutamate analogues", Brain Research, 604, 86–69 (1993).
Hon, Chang, and Gong, "Synthesis of (2S, 4S) and (2S, 4R)–4–Substituted Glutamic Acid Analogues For Neuroexcitatory Activity Studies", Heterocycles, 31, 191–195 (1990).
Baldwin, et al., "Stereospecific Amino Acid Synthesis; Preparation of the γ–Anion derived from Glutamic Acid", J. Chem. Soc., Chem. Commun, 828–829 (1988).
Cunningham J. Physiol (London) 1985 366. 46–62 [Abstract].

Primary Examiner—Joseph Conrad
Attorney, Agent, or Firm—Martin A. Hay; David E. Boone

[57] ABSTRACT

The present invention provides novel compounds that affect excitatory amino acid receptors and are useful in the treatment of neurological disorders. This invention also provides synthetic methods for the preparation of the novel compounds.

26 Claims, No Drawings

EXCITATORY AMINO ACID RECEPTOR ANTAGONISTS

CROSS REFERENCE

This application is a continuation-in-part of U.S. application Ser. No. 08/161,830 filed Dec. 3, 1993 now abandoned.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), a-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Antagonists of these receptors are useful for the treatment of acute and chronic neurodegenerative conditions, and as antipsychotic, anticonvulsant, analgesic, anxiolytic, antidepressant, and anti-emetic agents.

SUMMARY OF THE INVENTION

The present invention provides compounds that affect the excitatory amino acid receptors. More specifically, the present invention relates to compounds of the formula

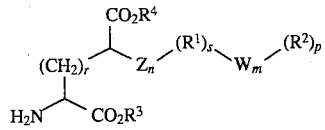

wherein:

Z is $NR^5$, O, or S;

W is $CH_{(3-p)}$, $-(CH_2)_q-$, $-(CH)_qCH_{(3-p)}$, $-(CH_2)_qCO-$, $-(CH_2)_qO-$, $-(CH_2)_qCH=CH(CH_2)_q-$, $-(CH_2)_qCH=CH-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

n is 0 or 1; m is 0 or 1; p is 0, 1, 2, or 3; q is 0–6; r is 1 or 2; s is 0 or 1, provided that the sum of n, m, p and s is at least 1;

$R^1$ and $R^2$ are independently aryl, substituted aryl, heterocycle, or substituted heterocycle;

$R^3$ is hydrogen or a carboxy protecting group;

$R^4$ is hydrogen or a carboxy protecting group;

$R^5$ is hydrogen, $C_1$–$C_{10}$ alkyl, acyl, or $SO_2$ ($C_1$–$C_4$ alkyl);

$R^6$ is $C_1$–$C_{10}$ alkyl;

provided that when n is 0 and s is 1, $R^1$ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl;

further provided that when n is 1, m is 1, and W is $NR^5$, O, S, SO, or SO2, s is 1; and when n is 0 and s is 0, m is 1 and W is $-(CH_2)_qCO-$, $-(CH_2)_qO-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

or a pharmaceutically-acceptable salt thereof.

The invention also provides pharmaceutical formulations comprising a compound of formula I in combination with one or more pharmaceutically-acceptable carriers, diluents, or excipients.

The present invention also provides processes for the preparation of compounds of the formula

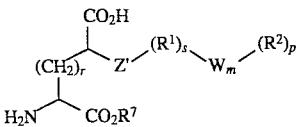

wherein:

Z' is O, or S;

W is $CH_{(3-p)}$, $-(CH_2)_q-$, $-(CH_2)_qCH_{(3-p)}$, $-(CH_2)_qCO-$, $-(CH_2)_qO-$, $-(CH_2)_qCH=CH(CH_2)_q-$, $-(CH_2)_qCH=CH-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

m is 0 or 1; p is 0, 1, 2, or 3; q is 0–6; r is 1 or 2; s is 0 or 1;

$R^1$ and $R^2$ are independently aryl, substituted aryl, heterocycle, or substituted heterocycle;

R⁷ is hydrogen or a carboxy protecting group;

provided that when m is 1 and W is NR⁵, O, S, SO, or SO₂, s is 1;

which comprises (1) reacting a compound of the formula

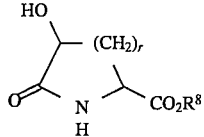

wherein R⁸ is a carboxy protecting group and r is 1 or 2, with a coupling reagent and a compound of the formula HZ'R¹W_m(R²)_p, wherein Z', R¹, W, R², m and p are as defined previously, to produce a 3-substituted pyroglutamate derivative; and (2) hydrolyzing said 3-substituted pyroglutamate derivative.

The present invention also provides processes for the preparation of compounds of the formula

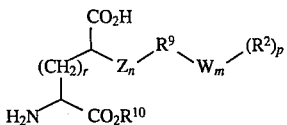

wherein:

n is 0;

W is CH_{(3-p)}, —(CH₂)_q—, —(CH₂)_qCH_{(3-p)}, —(CH₂)_qCO—, —(CH₂)_qO—, —(CH₂)_qCH=CH(CH₂)_q—, —(CH₂)_qCH=CH—, —CH=CHCO—, —CH=CHCOR⁶, —(CH₂)_qCHOHR⁶, —(CH₂)_qCHOH—, —(CH₂)_qCOR⁶, —O(CH₂)_q—, NR⁵, O, S, SO, or SO₂;

m is 0 or 1; p is 0, 1, 2, or 3; q is 0–6; r is 1 or 2;

R² is aryl, substituted aryl, heterocycle, or substituted heterocycle;

R⁹ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thidiazolyl, rhodaninyl, hydantoinyl, and pseudothiohydantoinyl; and R¹⁰ is hydrogen or a carboxy protecting group;

which comprises (1) reacting a compound of the formula

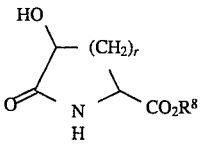

wherein R⁸ is a carboxy protecting group and r is 1 or 2, with a coupling reagent and a compound of the formula HR⁹W_m(R²)_p, wherein W, R², R⁹, m, and p are as defined previously, to produce a 3-substituted pyroglutamate derivative; and (2) hydrolyzing said 3-substituted pyroglutamate derivative.

The present invention also provides processes for the preparation of compounds of the formula

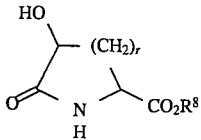

wherein R⁸ is a carboxy protecting group and r is 1 or 2, which comprises;

(1) cycloadding cyclopentadiene or cyclohexadiene and a nitroso compound of the formula

wherein R¹¹ is benzyl or substituted benzyl, to produce a compound of the formula

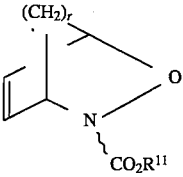

wherein R¹¹ and r are as defined above;

(2) oxidizing said formula V compound to produce a compound of the formula

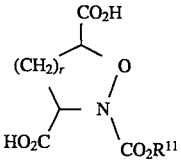

wherein R¹¹ and r are as defined above;

(3) protecting the carboxy groups of said formula VI compound to produce a compound of the formula

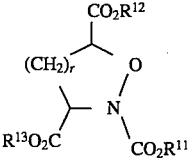

wherein

R¹¹ and r are as defined above; and

R¹² and R¹³ are carboxy protecting groups; and (4) deprotecting the nitrogen of said formula VII compound.

Further aspects of the present invention include a method of affecting one or more excitatory amino acid receptors, as well as methods of treating a neurological disorder which has been linked to the excitatory amino acid receptors, which comprises administering a compound of formula I. Examples of neurological disorders that are treated with a formula I compound include cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, cognitive disorders, idiopathic and drug-induced Parkinson's Disease, anxiety, emesis, brain edema, chronic pain, and tardive diskinesia. The formula I compounds are also useful as analgesic and antidepressant agents.

DETAILED DESCRIPTION OF THE INVENTION

The term "$C_1$–$C_{10}$ alkyl" represents a straight, branched, or cyclic alkyl chain having from one to ten carbon atoms. Typical straight or branched $C_1$–$C_{10}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, and the like. The term "$C_1$–$C_{10}$ alkyl" includes within it the terms "$C_1$–$C_6$ alkyl", and "$C_1$–$C_4$ alkyl". Typical cyclic $C_1$–$C_{10}$ alkyl groups include cyclopropyl, cyclobutyl, cyclopentyl, cyclohexyl, cycloheptyl, and the like. Typical $C_1$–$C_6$ alkyl groups include methyl, ethyl, n-propyl, isopropyl, n-butyl, isobutyl, sec-butyl, t-butyl, n-pentyl, isopentyl, and n-hexyl.

The term "acyl" represents a hydrogen or a $C_1$–$C_6$ alkyl group attached to a carbonyl group. Typical acyl groups include formyl, acetyl, propionyl, butyryl, valeryl, and caprolyl.

The term "carboxy protecting group" as used herein refers to one of the ester derivatives of the carboxylic acid group commonly employed to block or protect the carboxylic acid group while reactions are carried out on other functional groups. The protection of carboxylic acid groups is generally described in McOmie, *Protecting Groups in Organic Chemistry*, Plenum Press, N.Y., 1973, and Greene and Wuts, *Protecting Groups in Organic Synthesis*, 2nd. Ed., John Wiley & Sons, N.Y., 1991. Examples of such carboxy protecting groups include $C_1$–$C_6$ alkyl, aryl ($C_1$–$C_3$)alkyl, silyl and alkenyl groups such as methyl, ethyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl, t-butyl, t-amyl, trityl, trimethylsilyl, t-butyldimethylsilyl, allyl, 1-(trimethylsilylmethyl)-prop-1-en-3-yl, and the like.

The term "nitrogen protecting group" as used herein refers to substituents on amino groups that are commonly employed to block or protect the amino functionality. The protection of amino groups is generally described in McOmie, *Protecting Groups in Organic Chemistry*, Plenum Press, N.Y., 1973, and Greene and Wuts, *Protecting Groups in Organic Synthesis*, 2nd. Ed., John Wiley & Sons, N.Y., 1991. Examples of nitrogen protecting groups include benzyl, t-butyl, t-butyldimethylsilyl, triphenylsilyl, formyl, trityl, phthalimido, trichloroacetyl, chloroacetyl, benzyloxycarbonyl, methoxycarbonyl, 2-methylbenzyloxycarbonyl, 2,2,2-trichloroethoxycarbonyl, and the like.

The term "aryl" represents an aromatic radical, such as phenyl, and polynuclear aromatic radicals, such as naphthyl (e.g. 1-naphthyl or 2-naphthyl), fluorenyl (e.g. 2-fluorenyl), anthracyl, and phenanthryl. The term "substituted aryl" represents an aryl group substituted with one or more moieties chosen from the group consisting of halogen, hydroxy, cyano, nitro, $C_1$–$C_6$ alkyl $C_7$–$C_{10}$ alkyl, $C_3$–$C_6$ cycloalkyl, $C_1$–$C_4$ alkoxy, carboxy, acetyl, formyl, carboxymethyl, hydroxymethyl, amino, aminomethyl, or trifluoromethyl or an aryl group which is disubstituted or two adjacent carbon atoms by a $C_3$–$C_{10}$ alkylene, $C_2$–$C_{10}$ alkyleneoxy, $C_1$–$C_{10}$ alkylenedioxy, $C_5$–$C_6$ cycloalkylene or $C_5$–$C_6$ cycloalkyleneoxy group which, together with two adjacent carbon atoms in the aryl ring to which it is attached, forms a ring. Illustrative examples of a substituted aryl group include the following: 4-methylphenyl, 2-methylphenyl, 4-methoxyphenyl, 4-(i-propyl)phenyl, 4-cyclopentylphenyl, 4-(1,1,4,4-tetramethylbutyl)phenyl, 4-acetylphenyl, 4-trifluoromethylphenyl, 4-chlorophenyl, 3,4-dichlorophenyl, 2-bromophenyl, 3-iodophenyl, 6-bromonaphthyl, 3,4-methylenedioxyphenyl, indan-5-yl, 1,2,3,4-tetrahydronaphth-5-yl, and 1,1,4,4-tetramethyl-1,2,3,4-tetrahydronaphth-6-yl.

The term "substituted phenyl" represents a phenyl group substituted with one or more moieties chosen from the group consisting of halogen, cyano, nitro, $C_1$–$C_6$ alkyl, $C_1$–$C_4$ alkoxy, carboxy, acetyl, formyl, carboxymethyl, hydroxymethyl, amino, aminomethyl, or trifluoromethyl.

The term "heterocycle" represents a five-membered or six-membered ring, containing one to four heteroatoms, selected from oxygen, sulfur, and nitrogen, optionally fused to a second five-membered or six-membered ring, containing one to four heteroatoms, selected from oxygen, sulfur, and nitrogen. One skilled in the art will readily recognize that the remaining atoms of the ring are carbon atoms. These five-membered or six-membered rings may be saturated or unsaturated. Examples of a heterocycle group include thienyl, furyl, pyrrolyl, imidazolyl, pyrazolyl, thiazolyl, thiazolidinyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, pyrrolidinyl, piperidinyl, piperazinyl, pyrazolidinyl, pyrimdinyl, imiazolidinyl, morpholinyl, pyranyl, furanyl, thiomorpholinyl, 1,2,4-triazine-3,5-dionyl, pyrazolonyl, pteridinyl, xanthinyl, rhodaninyl, pseudothiohydantoinyl, hydantoinyl, and purinyl.

The term "substituted heterocycle" represents a heterocycle group substituted with one or more moieties chosen from the group consisting of halogen, hydroxy, cyano, nitro, $C_1$–$C_6$ alkyl, $C_1$–$C_4$ alkoxy, alkoxycarbonyl, carboxy, carboxymethyl, hydroxymethyl, amino, aminomethyl, or trifluoromethyl. Furthermore, the heterocycle group can optionally be fused to one or two aryl groups to form such benzo-fused groups as benzoxazolyl, benzisoxazolyl, benzofuranyl, benzothiazolyl, thianaphthenyl, benzothiazolyl, benzimidazolyl, indolyl, dibenzofuranyl, dibenzothiophenyl, and the like. Illustrative examples of a substituted heterocycle group include the following: 1,2,3,4-tetrahydrodibenzofuranyl, 2-methylbenzofuranyl, and 3,5-dimethylisoxazolyl.

For the purpose of providing clarity, the group $Z_n(R^1)_s W_m(R^2)_p$, wherein Z is O and n is 1, includes the following illustrative representatives:

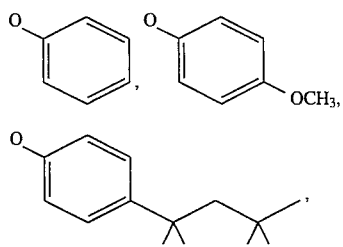

7
-continued
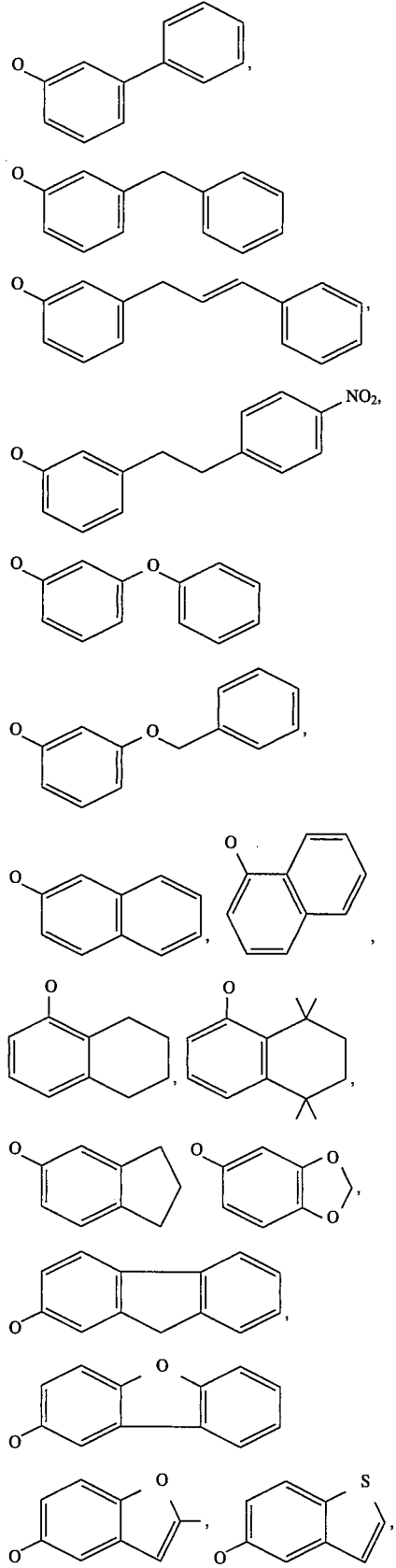
8
-continued
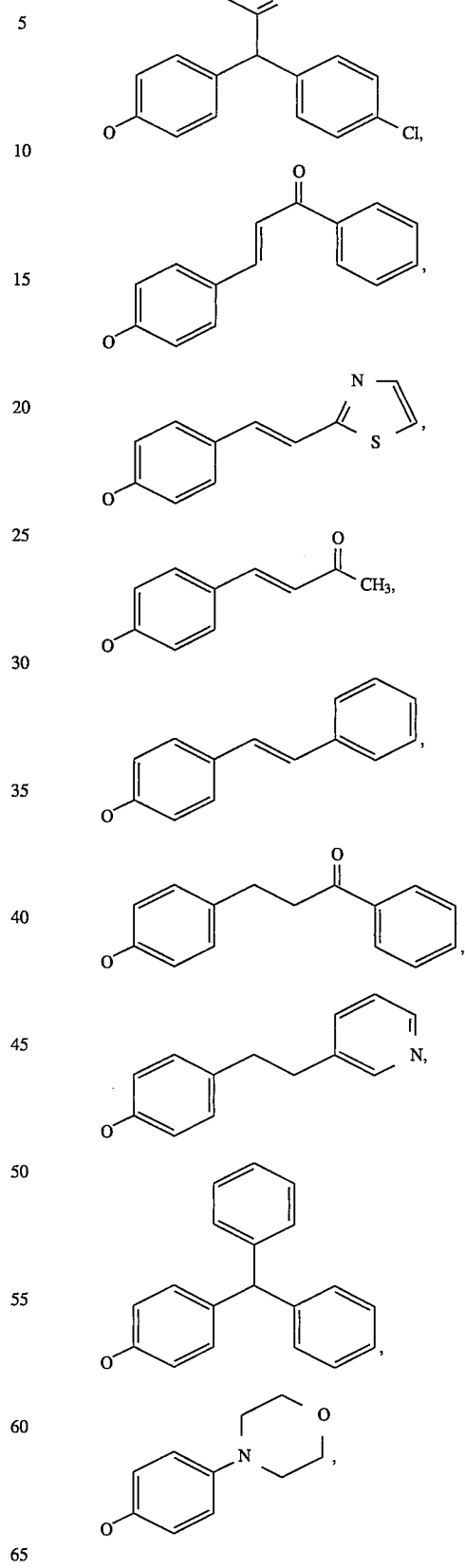

5,576,323
9
-continued
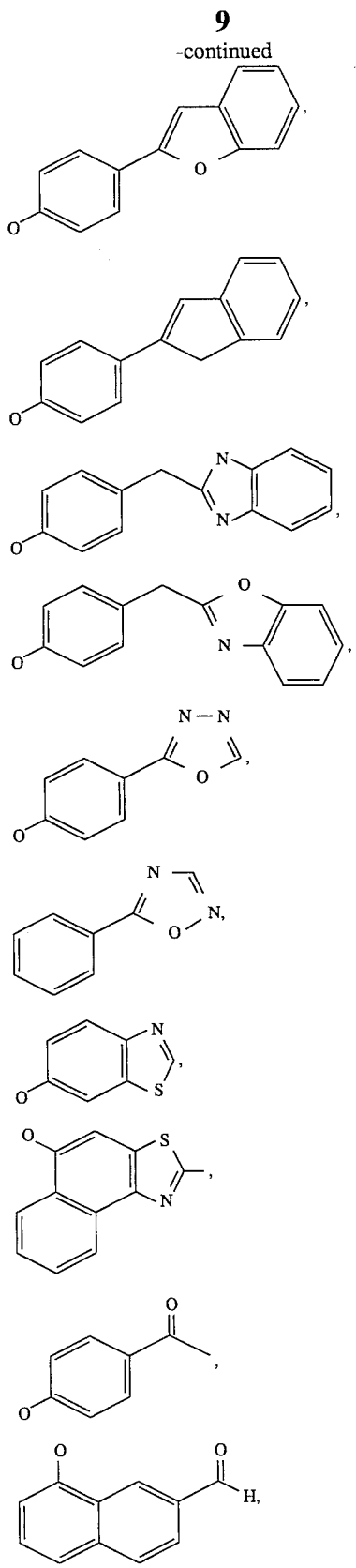
10
-continued
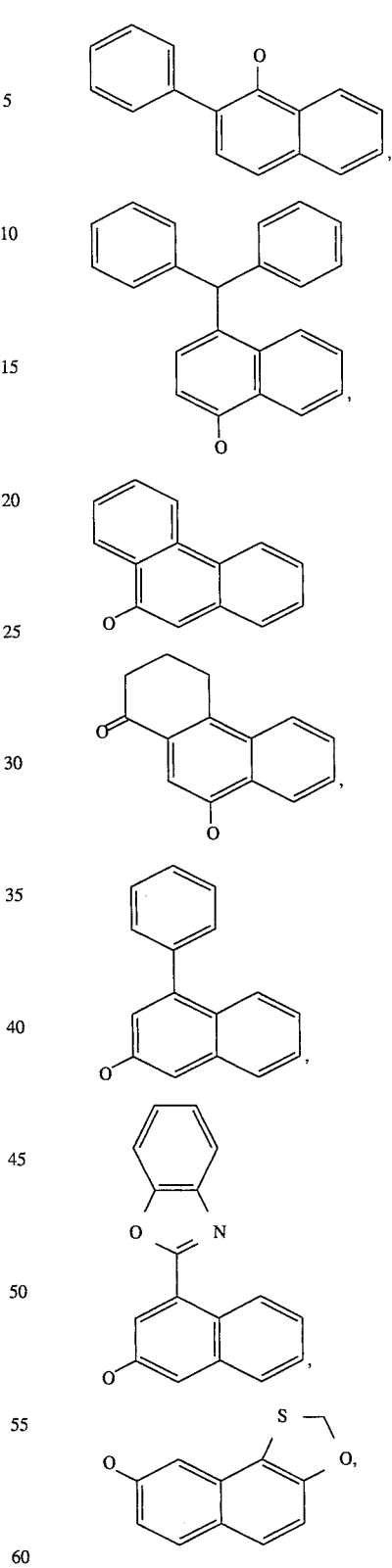

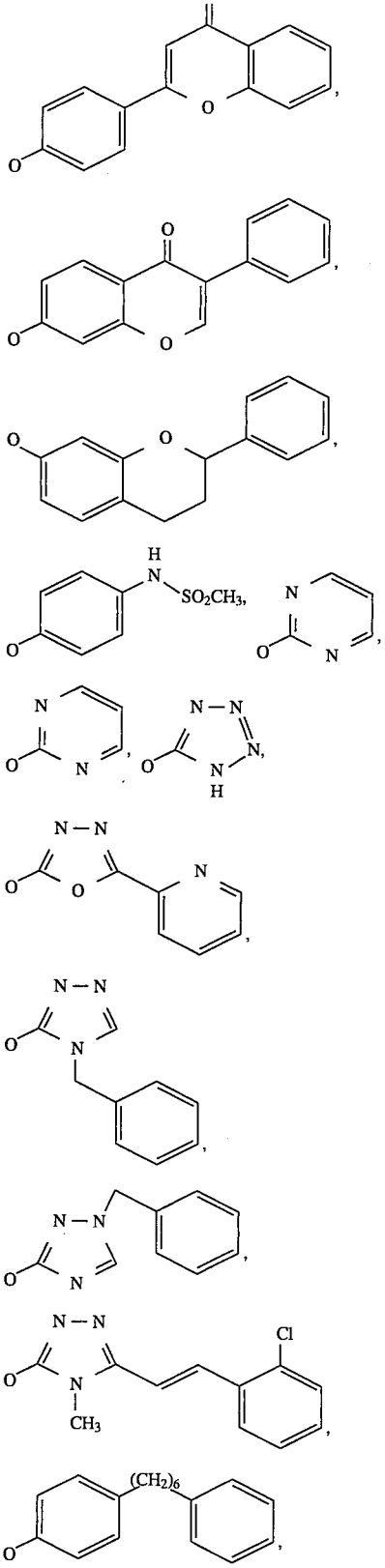

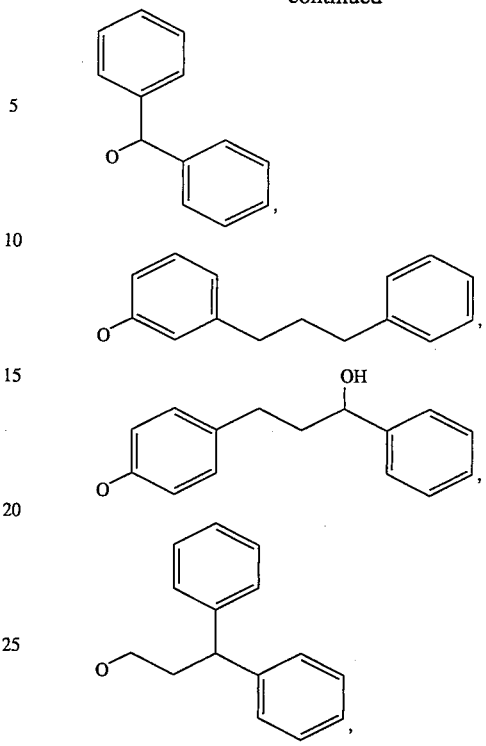

The present invention also includes those compounds wherein Z is a sulfur or a $NR^5$ group.

The term "affecting" refers to a formula I compound acting as an agonist, a partial agonist, or an antagonist at one or more excitatory amino acid receptors. The term "excitatory amino acid receptor" refers to ionotropic glutamate receptors, receptors that are directly coupled to the opening of ion channels in the cell membrane of neurons, and to metabotropic glutamate receptors, receptors that are coupled to cellular effectors via GTP-binding proteins. The term "NMDA excitatory amino acid receptor" refers to an ionotropic glutamate receptor that is selectively activated by N-methyl-D-aspartate (NMDA).

The term "neurological disorder" refers to both acute and chronic neurodegenerative conditions, including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, perinatal hypoxia, cardiac arrest, hypoglycemic neuronal damage, ocular damage and retinopathy, cognitive disorders, idiopathic and drug-induced Parkinson's Disease. This term also includes other neurological conditions that are caused by glutamate disfunction, including muscular spasms, migraine headaches, urinary incontinence, psychosis, opiate tolerance and withdrawal, anxiety, emesis, brain edema, chronic pain, convulsions, and tardive diskinesia.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I, wherein $R^3$ and/or $R^4$ is hydrogen.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, a-hydroxybutyrate, glycolate, maleate, tartrate, methanesulfonate, propanesulfonate, naphthalene-1-sulfonate, napthalene-2-sulfonate, mandelate, magnesium, tetramethylammonium, potassium, trimethylammonium, sodium, methylammonium, calcium, and the like salts.

A particular group of compounds of formula I is that in which

Z is O or S;
W is $-(CH_2)_qCH=CH-$, $-(CH_2)_q-$, $-(CH_2)_qO-$, $-(CH_2)_qCH=CH(CH_2)_q-$, $-O(CH_2)_q-$; and (i) n is 0, s is 1, m is 0, p is 0 and $R^1$ is tetrazolyl or triazolyl;

(ii) n is 1, s is 1, m is 0, p is 0 and $R^1$ is phenyl or naphthyl which is unsubstituted or substituted by one or two substituents chosen from the group consisting of halogen, hydroxy, cyano, nitro, $C_1-C_6$ alkyl, $C_7-C_{10}$ alkyl, $C_3-C_6$ cycloalkyl, $C_1-C_4$ alkoxy, carboxy, acetyl, formyl, carboxymethyl, hydroxymethyl, amino, aminomethyl and trifluoromethyl, or is disubstituted on two adjacent carbon atoms by a $C_3-C_{10}$ alkylene, $C_2-C_{10}$ alkylenoxy, $C_1-C_{10}$ alkylenedioxy, $C_5-C_6$ cycloalkylene or $C_5-C_6$ cycloalkyleneoxy group which, together with the two adjacent carbon atoms in the aryl ring to which it is attached forms a ring; or pyrimidyl or 1-methyltetrazol-5-yl; or (iii) n is 1, s is 1, m is 0 or 1, p is 1 or 2, $R^1$ is phenyl or triazolyl and each $R^2$ is selected independently from pyridyl and phenyl which is unsubstituted or substituted by one or two substituents chosen from the group consisting of halogen, hydroxy, cyano, nitro, $C_1-C_6$ alkyl, $C_7-C_{10}$ alkyl, $C_3-_6$ cycloalkyl, $C_1-C_4$ alkoxy, carboxy, acetyl, formyl, carboxymethyl, hydroxymethyl, amino, aminomethyl and trifluoromethyl; and q is 0 to 6;
r is 1; and
$R^3$ and $R^4$ are each hydrogen.

A more particular group of compounds of formula I is that in which

Z is O or S;
W is $-CH=CH-$, $-(CH_2)CH=CH,-$ $-(CH_2)_3-$ $-(CH_2)_4-$, $-(CH_2)_6-$, O or $-CH_2O-$; and (i) n is 0, s is 1, m is 0, p is 0 and $R^1$ is tetrazol-1-yl, tetrazol-2-yl or 1,2,4-triazol-2-yl;

(ii) n is 1, s is 1, m is 0, p is 0 and $R^1$ is phenyl, 2-methylphenyl, 4-methylphenyl, 4-methoxyphenyl, 4-isopropylphenyl, 4-cyclopentylphenyl, 4-(1,1,4,4-tetramethylbutyl) phenyl, 4-acetylphenyl, 4 -trifluoromethylphenyl, 4-chlorophenyl, 2-bromophenyl, 3-iodophenyl, 1-naphthyl, 2-naphthyl, 6-bromonaphth-2-yl, 1,6-dibromonaphth-2-yl, 3,4-methylenedioxyphenyl, indan-5-yl, 1,2,3,4-tetrahydronaphthyl, 1,1,4,4-tetramethyl-1,2,3,4-tetrahydronaphthyl, fluoren-2-yl, dibenzofuran-2-yl, 5,6,7,8-tetrahydrodibenzofuran-2-yl, 2-methylbenzofuran-5-yl, benzothiophen-5-yl, pyrimidin-2-yl or 1-methyltetrazol-5-yl; or (iii) n is 1, s is 1, m is 0 or 1, p is 1 or 2, $R^1$ is phenyl or 1,2,4-triazol-2-yl and each $R^2$ is selected independently from 2-pyridyl, phenyl, 2-chlorophenyl, 4-chlorophenyl, and 4-nitrophenyl;

r is 1; and
$R^3$ and $R^4$ are each hydrogen.

While all the formula I compounds of the present invention are believed to affect the metabotropic excitatory amino acid receptors and the NMDA excitatory amino acid receptors, certain compounds of the invention are preferred for such use. Preferably, Z is O or S; n is 1; s is 1; $R^1$ is aryl, substituted aryl, heterocycle, or substituted heterocycle; m is 0 or 1; W is $-(CH_2)_qO-$, $-(CH_2)_qCH=CH-$, $-(CH_2)_qCH=CH(CH_2)_q-$, $-(CH_2)_q-$, or $-O(CH_2)_q-$; q is 0-6; p is 0 or 1; and $R^2$ is aryl, substituted aryl, heterocycle, or substituted heterocycle.

Certain compounds of the present invention are more preferred for use in affecting the metabotropic excitatory amino acid receptors and/or the NMDA excitatory amino acid receptors. More preferably, Z is O, r is 1, $R^1$ is aryl or substituted aryl, $R^2$ is phenyl or substituted phenyl, and $R^3$ and $R^4$ are hydrogen. Representative compounds from this more preferred group of compounds include: 4-(4-phenylphenoxy)glutamic acid, 4-(3-phenylphenoxy)glutamic acid, 4-(4-benzyloxyphenoxy)glutamic acid, 4-(1,6-dibromo-2 -naphthyloxy)glutamic acid, 4-(1-naphthyloxy) glutamic acid, 4-(5-indanyloxy)glutamic acid, 4-(2-methyl-5-benzofuranyloxy)glutamic acid, and 4-(5-benzothiophenyloxy) glutamic acid.

Certain compounds of the invention are most preferred for use in affecting the metabotropic excitatory amino acid receptor and/or the NMDA excitatory amino acid receptor. Most preferably, the formula I compound is selected from the group consisting of 4-(4-methylphenoxy)glutamic acid, 4-(4-( 6 -phenylhexyl)phenoxy)glutamic acid, 4-(4-(3-phenylprop-2-enyl)phenoxy) glutamic acid, 4-(2-naphthyloxy) glutamic acid, 4-(6-bromo-2-naphthyloxy) glutamic acid, 4-(4-(2-(4-nitrophenyl) ethenyl)phenoxy)glutamic acid, 4-(2-fluorenoxy) glutamic acid, 4-(2-dibenzofuranoxy) glutamic acid, and 4-(5,6,7,8-tetrahydro-2-dibenzofuranoxy)glutamic acid.

The formula I compounds of the present invention have at least two asymmetric carbon atoms.

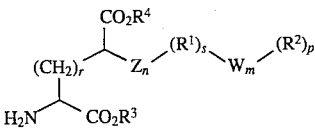

I

The asymmetric centers are the carbon atom bearing the $NH_2$ group (2) and the carbon atom bearing the $Z_n(R^1)_sW_m(R^2)_p$ group (4 or 5). As such, the compounds can exist as diastereomers, as enantiomers, or as a racemic modification (e.g. racemate). The present invention includes each enantiomer or diastereomer, mixtures of enantiomers (including racemates), and mixtures of diastereomers. When r is 1, the configurations for the preferred diastereomers are 2S,4R and 2S,4S. When r is 2, the configurations for the preferred diastereomers are 2S,5R and 2S,5S. The preferred racemates are 2SR,4RS and 2SR,4SR for the compounds wherein r is 1. The preferred racemates are 2SR,5RS and 2SR,5SR for the compounds wherein r is 2. The configuration of the most preferred stereoisomer is 2S,4S or 2S,5S, as shown below:

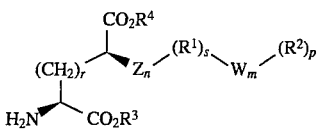

The formula I compounds of the present invention are synthesized from the formula IV compounds. Syntheses of the formula IV compounds, wherein r is 1, have been described in the literature. See Ohta, Hosoi, and Nozoe, *Tetr. Lett.*, 29, 329 (1988) and Yong Kyun Lee and Takeo Kaneko., *Bull. Chem. Soc. Jap.* 1973, vol. 46, no. 11, 3494–3498. An improved synthesis of the intermediate formula IV compounds from cyclopentadiene or cyclohexadiene is shown in Scheme I.

Scheme I

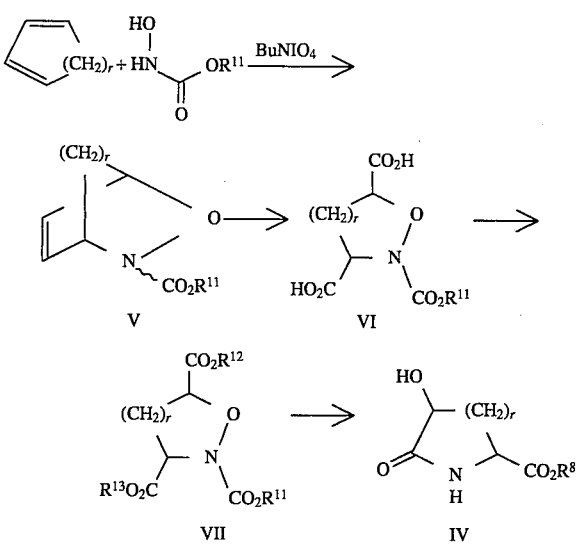

Generally, the formula V compounds are prepared by cycloaddition of cyclopentadiene or cyclohexadiene with a nitroso compound of the formula $ONCO_2R^{11}$. The cycloadduct is oxidized to provide a dicarboxylic acid, a compound of the formula VI. The free carboxylic acid groups are protected to provide the fully protected intermediate VII. The protecting group on the nitrogen is then removed under conditions suitable for cyclization to a compound of formula IV. One aspect of the present invention is an improved process for the synthesis of intermediate IV. The formula V compound is prepared by the reaction of cyclopentadiene or cyclohexadiene with a dienophile, a nitrosoformate ester. The nitrosoformate is prepared in situ by oxidation of an N-hydroxycarbamate. The N-hydroxycarbamate is prepared using procedures substantially as described in *Helv. Chim. Acta*, 70, 554 (1987). The reaction is preferably carried out by adding a suspension or a solution of the oxidizing agent to a cold solution containing the N-hydroxycarbamate and the diene. Suitable oxidizing agents for preparation of the dieneophile include tetrabutylammonium periodate, sodium periodate, potassium periodate, and the like. The preferred oxidizing agent for this oxidation is tetrabutylammonium periodate. Suitable solvents for this reaction are organic solvents, such as methylene chloride or chloroform. The reaction is typically carried out at a temperature of about −20° C. to about 0° C., preferably at −5° C. The reaction is quenched by the careful addition of 10% aqueous sodium bisulfate solution. The formula V compound is conveniently purified using silica-gel flash chromatography.

The formula V compound is oxidized to prepare the dicarboxylic acid intermediate (VI). Suitable oxidizing agents for this transformation include ozone, osmium tetroxide/sodium periodate, and potassium permanganate. The preferred oxidizing agent for this transformation is potassium permanganate. The oxidation is typically carried out as a two-phase mixture, comprising an organic phase containing the formula V compound and an inorganic phase containing potassium permanganate. A phase-transfer catalyst, such as tetrabutylammonium hydrogen sulfate, may be added to facilitate the transfer of the oxidizing agent to the organic phase. The reaction is typically carried out in an ice bath to maintain the temperature of the reaction between about 15° C. and about 30° C., preferably between about 18° C. and about 27° C. Suitable solvents for the organic phase include toluene, xylene, and benzene. The oxidation is typically complete after about one hour. The product of the reaction, after separation of the phases and removal of the inorganic material by extraction, is used in the next step without further purification.

The free carboxylic acid groups of the formula VI compound are protected to produce the formula VII compound. Methods for the protection of carboxyl groups are generally described in McOmie, *Protective Groups in Organic Chemistry*, Plenum Press, N.Y. 1973, and Greene and Wuts, *Protecting Groups in Organic Synthesis*, 2d. ed., John Wiley and Sons, N.Y., 1991. The ester protecting groups are preferred for use in the synthesis of the formula V compounds. The carboxylic acid groups may be protected as the $C_1$–$C_6$ alkyl, substituted alkyl, or aryl esters. The preferred ester is the $C_1$–$C_6$ alkyl ester; the methyl ester is the most preferred. This diester is prepared by the reaction of intermediate VI with trimethyloxonium tetrafluoroborate in the presence of an amine base. Suitable amine bases include triethylamine, N,N-diisopropylethylamine, N-methylmorpholine, and pyridine. The preferred amine base for use in this transformation is N,N-diisopropylethylamine. The reaction is typically carried out in an organic solvent, such as methylene chloride, at a temperature of about 25° C. to about 40° C., preferably below 33° C. The formula VII compound is purified using silica-gel flash chromatography.

The nitrogen protecting group of the formula VII compound is removed under conditions suitable for intramolecular cyclization to produce the formula IV compound. When the nitrogen protecting group is a benzyloxycarbonyl group, this transformation is easily accomplished using catalytic hydrogenation. Suitable catalysts for the removal of the nitrogen protecting group include palladium on carbon, platinum on carbon, palladium on alumina, platinum oxide, rhodium on alumina, or rhodium on carbon. The preferred catalyst for this transformation is 10% palladium on carbon. Suitable solvents for the reaction include polar organic solvents, such as tetrahydrofuran, ethyl acetate, methanol, and ethanol. Tetrahydrofuran is the preferred solvent for the reaction. The reduction is carried out at a hydrogen pressure of about 45 psi to about 60 psi and at a temperature of about 20° C. to about 40° C., preferably at room temperature. The catalyst may be removed by filtration and the formula IV compound purified using silica-gel flash chromatography and/or crystallization. The compounds of the present invention are chemically synthesized from intermediates of general formula IV by a number of different routes. The specific synthetic steps of the routes described herein may be combined in other ways to prepare the formula I compounds. The following discussion is not intended to be limiting to the scope of the present invention, and should not be so construed. The synthesis of the formula I compounds, wherein Z is oxygen or sulfur and n is one, is shown in Scheme II.

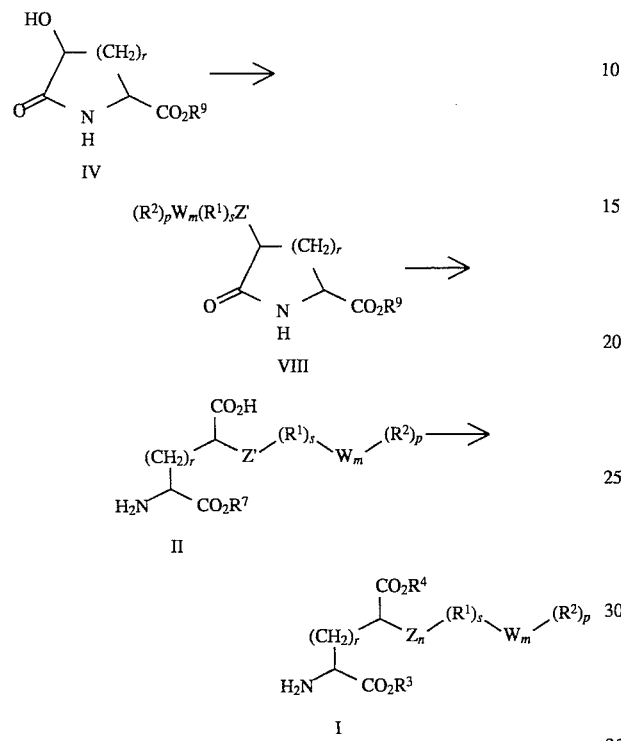

Scheme II

Generally, a formula IV compound is reacted with a coupling reagent and a compound of the formula $HZ'(R^1)_sW_m(R^2)_p$, wherein the variables $R^1$, W, $R^2$, m, s, and p are as defined previously, Z' is S or O, to produce a 3-substituted pyroglutamate derivative, a formula VIII compound. This intermediate is hydrolyzed to produce a compound of the formula II. The carboxylic acid groups of the formula II compound may optionally be modified or pharmaceutically-acceptable salts prepared to produce the formula I compounds.

More specifically, a formula IV compound is reacted with a compound of the formula $HZ'(R^1)_sW_m(R^2)_p$ to produce a 3-substituted pyroglutamate derivative, a compound of general formula VIII. The preferred coupling reagent for this reaction is the Mitsunobu reagent, prepared by the reaction of a dialkyl azodicarboxylate with triphenylphosphine. Mitsunobu, *Synthesis*, 1–28 (1981). A useful dialkyl azodicarboxylate for this reaction is diethyl azodicarboxylate. Preferably, a solution comprising a formula IV compound, triphenylphosphine, and a compound of the formula $HZ'(R^1)_sW_m(R^2)_p$ in an organic solvent, is treated with a diethyl azodicarboxylate solution. Suitable organic solvents for this reaction are anhydrous aprotic solvents, such as ether or tetrahydrofuran. The reaction is carried out at a temperature of about 0° C. to about 25° C., preferably at 5° C. initially. The reaction is usually complete after about 18 hours.

The formula VIII intermediate is then hydrolyzed to produce a compound of formula II, wherein $R^7$ is a carboxy protecting group or hydrogen. This hydrolysis is generally carried out using an inorganic base, such as lithium hydroxide or sodium hydroxide, in an aqueous/organic solvent mixture. A suitable solvent mixture for this reaction is a mixture of water and tetrahydrofuran. The hydrolysis is typically carried out at a temperature of about 25° C. to about 65° C., preferably at a temperature of about 60° C. to about 65° C.

The formula I compounds wherein $R^3$ and $R^4$ are other than hydrogen are prepared from the formula II compounds. These compounds are prepared using standard synthetic organic techniques. For example, the esters of the formula I compounds are prepared using procedures described in McOmie, *Protecting Groups in Organic Chemistry*, or Greene and Wuts, *Protecting Groups in Organic Synthesis*.

The synthesis of the formula I compounds, wherein n is 0, s is 1, and $R^1$ is a tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, or pseudothiohydantoinyl group, is shown in Scheme III.

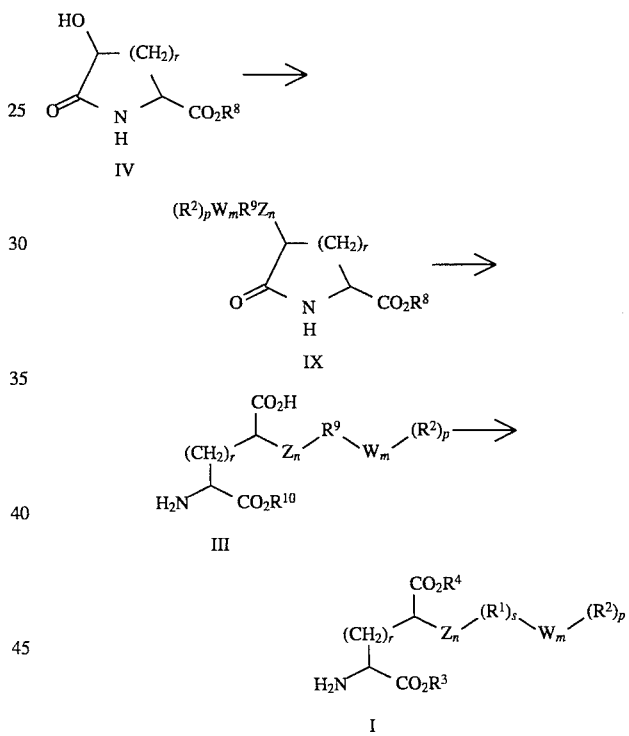

Scheme III

Generally, a formula IV compound is coupled with a tetrazolyl or triazolyl compound to produce a 3-substituted pyroglutamate derivative, a compound of general formula IX. This intermediate is hydrolyzed to produce the carboxylic acid compound of formula III. This compound is optionally esterified or a pharmaceutically acceptable salt prepared to produce a formula I compound.

More specifically, a formula IV compound is reacted with a coupling reagent and a compound of the formula $HR^9W_m(R^2)_p$, wherein $R^9$ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl, and the variables W, m, $R^2$, and p are as defined previously, to produce a 3-substituted pyroglutamate, a compound of the formula IX. A useful coupling reagent for this reaction is the Mitsunobu reagent, prepared by the reaction of a dialkyl azodicarboxylate with triphenylphosphine. Mitsunobu, *Synthesis*, 1–28 (1981). The preferred dialkyl azodicarboxylate for this reaction is diethyl azodicarboxylate. Preferably, a solution comprising a formula IV compound, triphenylphosphine, and a compound of the formula $HR^9W_m(R^2)_p$ in an organic solvent, is treated with a diethyl azodicarboxylate solution. Suitable organic solvents for this reaction are anhydrous aprotic solvents, such as ether or tetrahydrofuran. The reaction is carried out at a temperature of about 0° C. to about 25° C., preferably at 5° C. The reaction is usually complete after about 18 hours.

The formula IX intermediate is then hydrolyzed to produce a formula III compound, wherein $R^{10}$ is hydrogen or a carboxy protecting group. This hydrolysis is generally carried out using an inorganic base, such as lithium hydroxide or sodium hydroxide, in an aqueous/organic solvent mixture. A suitable solvent mixture for this reaction is a mixture of water and tetrahydrofuran. The hydrolysis is typically carried out at a temperature of about 25° C. to about 65° C., preferably at a temperature of about 60° C. to 65° C.

The formula I compounds wherein $R^3$ and $R^4$ are other than hydrogen are prepared from the formula III compounds. These compounds are prepared using standard synthetic organic techniques. For example, the esters of the formula I compounds are prepared using procedures described in McOmie, *Protecting Groups in Organic Chemistry*, or Greene and Wuts, *Protecting Groups in Organic Synthesis*.

The synthesis of the formula I compounds, wherein Z is O, n is 1, and s is 0, is shown in Scheme IV.

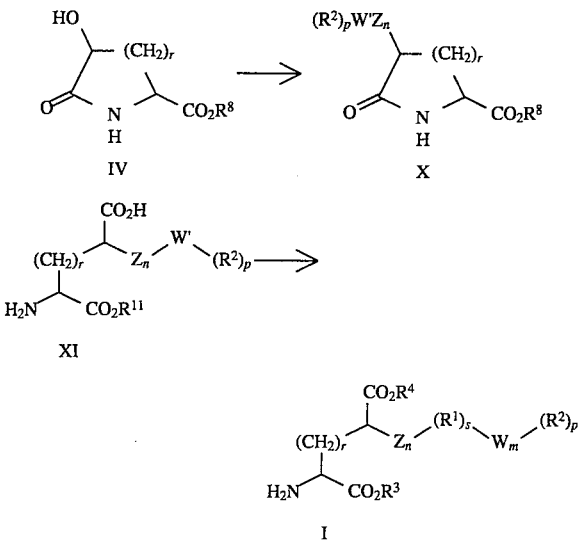

Generally, a formula IV compound is reacted with an alkylating reagent to produce a 3-substituted pyroglutamate derivative, a compound of general formula X, wherein Z is O, n is 1, and W' is $CH_{(3-p)}$, $-(CH_2)_q-$, $-(CH_2)_qCH_{(3-p)}$, $-(CH_2)_qCO-$, $-(CH_2)_qCH=CH-$, $-CH=CHCO-$, $-CH=CHCOR^6$, $-(CH_2)_qCHOHR^6$, $-(CH_2)_qCHOH-$, or $-(CH_2)_qCOR^6$. This intermediate is hydrolyzed to produce the carboxylic acid compound of formula XI. This compound is optionally esterified or a pharmaceutically acceptable salt prepared to produce a formula I compound.

More specifically, a formula IV compound is reacted with a compound of the formula $XW'(R^2)_p$, wherein X is a leaving group such as halide, triflate, mesylate, or rosylate, and the variables W', $R^2$, q, and p are as defined previously. Preferably, a solution comprising the formula IV compound and an amine base in an organic solvent is treated with a solution of the alkylating reagent. Suitable amine bases include triethylamine, N,N-diisopropylethylamine, N-methylmorpholine, and pyridine. The preferred amine base for use in this transformation is N,N-diisopropylethylamine. Suitable organic solvents for this reaction include methylene chloride, ether, tetrahydrofuran, and acetonitrile. The reaction is preferably carried out at a temperature of about 0° C. to about 80° C. When a triflate is used as the alkylating agent, the reaction is preferably carried out at a temperature of about 0° C. to about 20° C. When a halide is used as the alkylating agent, the reaction is preferably carried out at a temperature of about 25° C. to about 80° C.

The formula X intermediate is then hydrolyzed to produce a compound of the general formula XI, wherein $R^{11}$ is hydrogen or a carboxy protecting group. This hydrolysis is generally carried out using an inorganic base, such as lithium hydroxide or sodium hydroxide, in an aqueous/organic solvent mixture. A suitable solvent mixture for this reaction is a mixture of water and tetrahydrofuran. The hydrolysis is typically carried out at a temperature of about 25° C. to about 65° C., preferably a temperature of about 60° C. to about 65° C.

The formula I compounds, wherein $R^3$ and $R^4$ are other than hydrogen, are prepared from the formula XI compounds. These compounds are prepared using standard synthetic organic techniques. For example, the esters of the formula I compounds are prepared using procedures described in McOmie, *Protecting Groups in Organic Chemistry*, or in Greene and Wuts, *Protecting Groups in Organic Synthesis*.

The synthesis of the formula I compounds, wherein Z is S, n is 1, and s is 0, is shown in Scheme V.

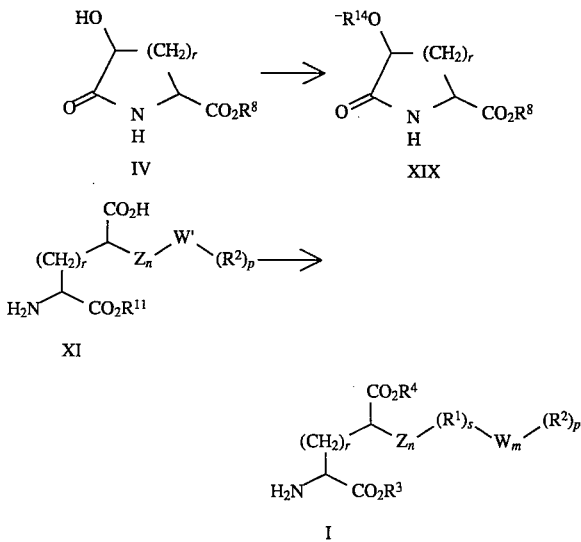

Generally, a formula IV compound is reacted with an alkylsulfonyl chloride, an alkylsulfonic anhydride, or arylsulfonyl chloride to produce an alkylsulfonate or arylsulfonate of formula XIX. This intermediate is then reacted with a compound of the formula $HZ_nW'(R^2)_p$, wherein Z is S, n is 1, and W', $R^2$, and p are as defined above. The product of this reaction is hydrolyzed to produce the carboxylic acid of formula XI. This compound is optionally esterified or a pharmaceutically acceptable salt prepared to produce a formula I compound.

More specifically, a formula IV compound is reacted with an alkylsulfonyl chloride, an alkylsulfonic anhydride, or an arylsulfonyl chloride in the presence of an amine base to produce a compound of formula XIX, wherein $R^{14}$ is an alkylsulfonyl or arylsulfonyl group, such as toluenesulfonyl, methanesulfonyl, or trifluoromethanesulfonyl. Examples of typical alkylsulfonyl chlorides, alkylsulfonic anhydrides, or arylsulfonyl chlorides are p-toluenesulfonyl chloride, methanesulfonyl chloride, and trifluoromethanesulfonic anhydride. Suitable amine bases for use in this transformation include triethylamine, N,N-diisopropylethylamine, pyridine, and dimethylaminopyridine. The reaction is typically carried out in a dry organic solvent, such as dry tetrahydrofuran or dry methylene chloride, at a temperature of about −78° C. to about 0° C. Preferably, a cold solution comprising the formula IV compound and an amine base in a dry organic solvent is treated with the alkylsulfonyl chloride, alkylsulfonic anhydride, or arylsulfonyl chloride.

The formula XIX intermediate is then reacted with a compound of the formula $HZ_nW'(R^2)_p$, wherein Z is S, n is 1, and W', $R^2$, and p are as defined above. This reaction is typically carried out in the presence of an amine base, such as triethylamine, N,N-diisopropylethylamine, pyridine, or dimethylaminopyridine. Suitable solvents for this reaction include methylene chloride, ether, tetrahydrofuran, and acetonitrile. The reaction is preferably carried out at a temperature of about −20° C. to about 50° C. When $R^{14}$ is a trifluoromethanesulfonyl group, the reaction is preferably carried out at a temperature of about −20° C. to about 0° C.

The product of this reaction is then hydrolyzed to produce a compound of the general formula XI, wherein $R^{11}$ is hydrogen or a carboxy protecting group. This hydrolysis is generally carried out using an inorganic base, such as lithium hydroxide or sodium hydroxide, in an aqueous/organic solvent mixture. A suitable solvent mixture for this reaction is a mixture of water and tetrahydrofuran. The hydrolysis is typically carried out at a temperature of about 25° C. to about 65° C., preferably a temperature of about 60° C. to about 65° C.

The formula I compounds, wherein $R^3$ and $R^4$ are other than hydrogen, are prepared from the formula XI compounds. These compounds are prepared using standard synthetic organic techniques. For example, the esters of the formula I compounds are prepared using procedures described in McOmie, *Protecting Groups in Organic Chemistry*, or in Greene and Wuts, *Protecting Groups in Organic Synthesis*.

The synthesis of the formula I compounds, wherein Z is $NR^5$ and n is 1, is shown in Scheme VI.

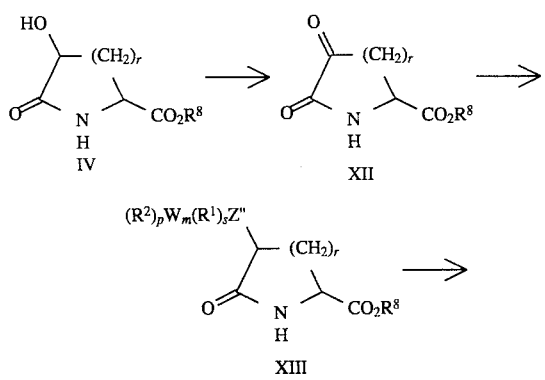

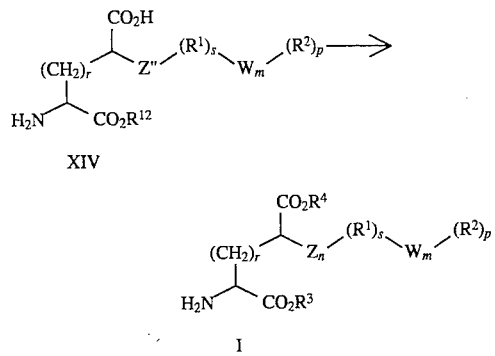

Generally, a formula IV compound is oxidized to a formula XII compound. This compound is reacted with an amine in the presence of a suitable reducing agent to give a formula XIII compound. This intermediate is hydrolyzed to produce a compound of formula XIV. The carboxylic acid groups of the formula XIV compound may optionally be modified or pharmaceutically acceptable salts prepared to produce the formula I compounds.

More specifically, a formula IV compound is oxidized with a suitable oxidizing agent to produce a 3-ketopyroglutamate derivative, a compound of general formula XII. The hydroxyl group is oxidized to the ketone with oxidizing reagents and methods that are well known in the chemical arts, such as the Swern oxidant or other dimethylsulfoxide (DMSO) based reagents. Mancuso, Huang, and Swern, *J. Org. Chem.*, 43, 2480–2482 (1978); Epstein, and Sweat, *Chem, Rev.*, 67, 247–260 (1967); and Smith, Leenay, Lin, Nelson and Ball, *Tetr. Lett.*, 29, 49–52 (1988). A preferred oxidizing reagent is a combination of oxalyl chloride and dimethylsulfoxide. Generally, dimethylsulfoxide and oxalyl chloride are combined in an organic solvent, such as methylene chloride, at about −78° C. to form the oxidizing agent. After about 5 minutes to about 15 minutes, a solution of the alcohol intermediate, the formula IV compound, is added to the cold oxidizing reagent solution. This mixture is then treated with N,N-diisopropylethylamine and the resulting mixture cooled to about −78° C. to about −50° C. The oxidization is quenched by the addition of saturated ammonium chloride solution.

The formula XIII compound is prepared by reductive amination of intermediate XII. The formula XII compound is reacted directly with a compound of the formula $HZ''(R^1)_sW_{m(R^2)_p}$, wherein Z'' is NH or $N(C_1-C_{10}$ alkyl), and $R^1$, $R^2$, W, s, m, and p are as defined previously, in the presence of a suitable reducing agent. Suitable reducing agents for this reaction include sodium cyanoborohydride and sodium borohydride; preferably sodium cyanoborohydride. The preferred solvent for this reaction is anhydrous methanol. The reaction is typically carried out at room temperature.

The formula XIII intermediate is then hydrolyzed to produce a formula XIV compound, wherein $R^{12}$ is hydrogen or a carboxy protecting group. This hydrolysis is generally carried out using an inorganic base, such as lithium hydroxide or sodium hydroxide, in an aqueous/organic solvent mixture. A suitable solvent mixture for this reaction is a mixture of water and tetrahydrofuran. The hydrolysis is typically carried out at a temperature of about 25° C. to about 65° C., preferably at a temperature of about 60° C. to about 65° C.

The formula I compounds, wherein $R^3$ and $R^4$ are other than hydrogen, are prepared from the formula XIV compounds using standard synthetic organic techniques. For example, the esters of the formula I compounds are prepared using procedures described in McOmie, *Protecting Groups in Organic Chemistry,* or in Greene and Wuts, *Protecting Groups in Organic Synthesis.*

Examples of compounds that have been prepared and are a part of this invention are listed in Table I.

TABLE I

Formula I Compounds

| No. | Z | R[1] | W | R[2] | n | m | p |
|---|---|---|---|---|---|---|---|
| 1 | O | phenyl | — | — | 1 | 0 | 0 |
| 2 | S | phenyl | — | — | 1 | 0 | 0 |
| 3 | O | 4-methylphenyl | — | — | 1 | 0 | 0 |
| 4 | o | 2-methylphenyl | — | — | 1 | 0 | 0 |
| 5 | O | 4-methoxyphenyl | — | — | 1 | 0 | 0 |
| 6 | O | 4-(isopropyl)phenyl | — | — | 1 | 0 | 0 |
| 7 | O | 4-cyclopentylphenyl | — | — | 1 | 0 | 0 |
| 8 | O | 4-(2,2,4,4-tetra-methylbutyl)phenyl | — | — | 1 | 0 | 0 |
| 9 | O | 4-acetylphenyl | — | — | 1 | 0 | 0 |
| 10 | O | 4-trifluoromethylphenyl | — | — | 1 | 0 | 0 |
| 11 | O | 3,4-dichlorophenyl | — | — | 1 | 0 | 0 |
| 12 | O | phenyl | — | 4-phenyl | 1 | 0 | 1 |
| 13 | O | phenyl | — | 3-phenyl | 1 | 0 | 0 |
| 14 | O | phenyl | 4-(CH$_2$) | phenyl | 1 | 1 | 1 |
| 15 | O | phenyl | 2-(CH$_2$) | phenyl | 1 | 1 | 1 |
| 16 | O | phenyl | 4-((CH$_2$)$_6$) | phenyl | 1 | 1 | 1 |
| 17 | O | phenyl | 4-(CH$_2$CHCH) | phenyl | 1 | 1 | 1 |
| 18 | O | phenyl | 4-(CH=CH) | 4-nitrophenyl | 1 | 1 | 1 |
| 19 | O | phenyl | 4-(O) | phenyl | 1 | 1 | 1 |
| 20 | O | phenyl | 4-(OCH$_2$) | phenyl | 1 | 1 | 1 |
| 21 | O | naphth-2-yl | — | — | 1 | 0 | 0 |
| 22 | O | 6-bromonaphth-2-yl- | — | — | 1 | 0 | 0 |
| 23 | O | 1,6-dibromonaphth-2-yl | — | — | 1 | 0 | 0 |
| 24 | S | naphth-2-yl | — | — | 1 | 0 | 0 |
| 25 | O | naphth-1-yl | — | — | 1 | 0 | 0 |
| 26 | O | 5,6,7,8-tetrahydro naphth-1-yl | — | — | 1 | 0 | 0 |
| 27 | O | 5,5,8,8-tetramethyl-6-7-dihydronaphth-2-yl | — | — | 1 | 0 | 0 |
| 28 | O | indan-5-yl | — | — | 1 | 0 | 0 |
| 29 | O | 3,4-methylene-dioxyphenyl | — | — | 1 | 0 | 0 |
| 30 | O | fluoren-2-yl | — | — | 1 | 0 | 0 |
| 31 | O | dibenzofuran-2-yl | — | — | 1 | 0 | 0 |
| 32 | O | 5,6,7,8-tetrahydro-dibenzofuran-2-yl | — | — | 1 | 0 | 0 |
| 33 | O | 2-methylbenzofuran-5-yl | — | — | 1 | 0 | 0 |
| 34 | O | benzothiaphen-5-yl | — | — | 1 | 0 | 0 |
| 35 | O | phenyl | 4-CH | pyridin-2-yl, 4-chlorophenyl | 1 | 1 | 2 |
| 36 | S | 1,2,4-triazol-3-yl | 4-CH$_2$ | phenyl | 1 | 1 | 1 |
| 37 | S | 1,2,4-triazol-3-yl | 1-CH$_2$ | phenyl | 1 | 1 | 1 |
| 38 | S | 1,2,4-triazol-3-yl | 5-CHCH | 2-chlorophenyl | 1 | 1 | 1 |
| 39 | S | pyrimidin-2-yl | — | — | 1 | 0 | 0 |
| 40 | S | 1-(N-methyl)-tetrazol-5-yl | — | — | 1 | 0 | 0 |
| 41 | — | 1,2,4-triazol-1-yl | — | — | 0 | 0 | 0 |
| 42 | — | tetrazol-2-yl | — | — | 0 | 0 | 0 |
| 43 | — | tetrazol-1-yl | — | — | 0 | 0 | 0 |
| 50 | 0 | phenyl | 4-((CH$_2$)$_3$) | — | phenyl | 1 | 1 |
| 51 | 0 | phenyl | 4-((CH$_2$)$_4$) | — | phenyl | 1 | 1 |

The formula I compounds are prepared stereospecifically as shown in Scheme VII.

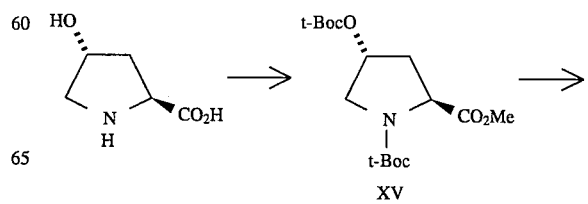

Scheme VII

-continued
Scheme VII

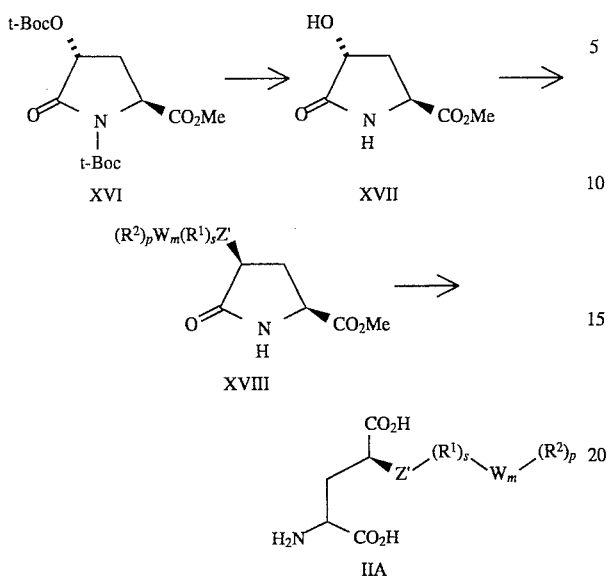

Generally, 4-hydroxy-L-proline is protected on the nitrogen, the carboxy group, and the hydroxy group. The fully protected compound is oxidized and partially deprotected to produce a formula XVII compound. The formula XVII compound is reacted with a coupling reagent and a compound of the formula $HZ'(R^1)_sW_m(R^2)_p$, wherein the variables $R^1$, W, $R^2$, m, s, and p are as defined previously, Z' is S or O, to produce a 3S,5S-3-substituted pyroglutamate derivative, a formula XVIII compound. This intermediate is hydrolyzed to produce a compound of formula IIA. The carboxylic acid groups of the formula IIA compound may optionally be modified or pharmaceutically-acceptable salts prepared to produce the formula I compounds.

More specifically, 4-hydroxy-L-proline is converted to its methyl ester using standard synthetic methodologies. Suitable methods for the formation of esters are described in McOmie, *Protecting Groups in Organic Chemistry* and Greene and Wutz, *Protecting Groups in Organic Synthesis.* The methyl ester is then converted to the fully protected derivative using standard synthetic techniques. The preferred protecting group is the t-butoxycarbonyl group (t-Boc). This compound is prepared by the reaction of 4-hydroxy-L-proline methyl ester with di-tert-butyldicarbonate in the presence of triethylamine and dimethylaminopyridine, to produce a formula XV compound.

The formula XVI compound is prepared by oxidation of the formula XV compound. A suitable oxidizing agent for this transformation is a mixture of ruthenium(IV) oxide and sodium periodate. This oxidation is carried out as a multiphase mixture, comprising an organic phase of the pyrrolidone compound (XV) in an organic solvent, such as ethyl acetate, an aqueous solution of the periodate salt, and ruthenium(IV) oxide. The reaction is typically complete after about two days.

The amino and hydroxy protecting groups of the formula XVI compound are removed to prepare the formula XVII compound. Both protecting groups are conveniently removed by treatment of the formula XVI compound with trifluoroacetic acid. This transformation is typically carried out at room temperature, and is generally complete after about one to about four hours.

The formula XVIII compound is then converted to the formula IIA compound using procedures substantially as described previously. See Scheme II and the discussion following the Scheme.

It will be appreciated that the processes described hereinabove for preparing the compounds of formula I all involve the same final stage hydrolysis of a compound of formula

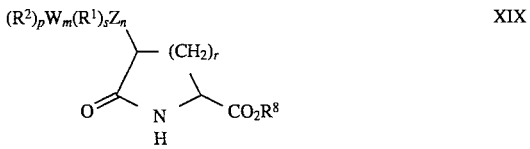

XIX in which $R^8$ represents a hydrogen atom or a carboxyl protecting group, for example a $C_1$–$C_6$ alkyl group such as methyl or ethyl, an aryl ($C_1$–$C_3$) alkyl group such as benzyl, a silyl group such as trimethylsilyl or an alkenyl group such as allyl.

According to another aspect, therefore, the invention provides a process for preparing a compound of formula I, or a pharmaceutically acceptable salt thereof, which comprises hydrolysing a compound of formula XIX.

The compounds of formula XIX are believed to be novel and accordingly are provided as a further aspect of the invention.

The formula I compounds of the present invention affect excitatory amino acid receptors. Specifically, the formula I compounds affect the metabotropic glutamate receptors and the NMDA excitatory amino acid receptors. Therefore, another aspect of the present invention is a method of affecting an excitatory amino acid receptor in mammals, which comprises administering to a mammal requiring modulated excitatory amino acid neurotransmission a pharmaceutically-effective amount of a compound of formula I. The term "pharmaceutically-effective amount" is used to represent an amount of the compound of the invention which is capable of affecting the excitatory amino acid receptors. By affecting, a compound of the invention may be acting as an antagonist, a partial agonist, or an agonist. When the compound acts as an antagonist, the compound blocks the EAA receptor, therefore, preventing the receptor from interacting with the natural ligand (i.e. L-glutamate). When a compound of the invention acts as an agonist, the interaction of the compound with the EAA receptor mimics the response of the interaction of this receptor with its natural ligand (i.e. L-glutamate).

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Hungington's Chorea, amyotrophic lateral sclerosis, AIDS-induced dementia, ocular damage and retinopathy, cognitive disorders, and idopathic and drug-induced Parkinson's. The present invention also provides methods for treating these disorders which comprises administering to a patient in need thereof an effective amount of a compound of formula I.

The formula I compounds of the present invention are also believed to have the ability to treat a variety of other neurological disorders in mammals that are associated with glutamate dysfunction, including muscular spasms, convulsions, migraine headaches, urinary incontinence, psychosis, opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I.

Experiments were performed to demonstrate the ability of the formula I compounds to affect the excitatory amino acid receptors. The affinity for metabotropic glutamate receptors was demonstrated by the selective displacement of 1S,3R-ACPD-sensitive [$^3$H]glutamate binding to rat brain cell membranes. The binding of [$^3$H]glutamate was conducted with crude membranes of rat forebrain as described by Schoepp and True. Schoepp and True, *Neuroscience Lett.*, 145, 100–104 (1992), True and Schoepp, *Society for Neuroscience Abstracts*, 19, 470 (1993) and Wright, McDonald and Schoepp, *J. Neurochem.* 63: 938–945, 1994. The percent displacement of [$^3$H]Glu, at a 100 µM concentration of the formula I compound, is shown in Table II.

TABLE II

| Receptor Binding of Formula I Compounds | |
|---|---|
| Compound No.[a] | Percent displacement of L—[$^3$H]Glu (100 µM) |
| 1 | 88.0 |
| 2 | 77.1 |
| 3 | 82.4 |
| 4 | 66.5 |
| 5 | 82.3 |
| 6 | 53.9 |
| 7 | 72.0 |
| 8 | 52.3 |
| 9 | 85.8 |
| 10 | 77.9 |
| 12 | 86.7 |
| 13 | 81.6 |
| 14 | 93.8 |
| 15 | 85.9 |
| 16 | 76.9[c] |
| 17 | 75.9 |
| 18 | 92.1 |
| 19 | 84.6 |
| 20 | 67.8 |
| 21 | 95.9 |
| 22 | 93.9 |
| 23 | 99.5 |
| 24[d] | 100.6[c] |
| 25 | 98.5 |
| 26 | 82.1 |
| 27 | 66.5 |
| 28 | 97.8 |
| 29 | 89.0 |
| 30 | 93.7 |

TABLE II-continued

| Receptor Binding of Formula I Compounds | |
|---|---|
| Compound No.[a] | Percent displacement of L—[$^3$H]Glu (100 µM) |
| 31 | 99.4 |
| 32 | 92.6 |
| 33 | 90.1 |
| 34 | 95.3 |
| 35 | 92.4 |
| 36 | 81.3 |
| 38 | 89.9 |
| 44[b] | 103.2 |
| 45[b] | 101.5 |
| 46[b] | 85.5 |
| 47[b] | 107.1 |
| 48 | 91.9 |
| 49 | 81.5 |
| 50 | 75.9 |
| 51 | 81.0 |

[a]Compounds tested as a mixture of enantiomers, unless otherwise noted.
[b]Compound tested as pure 2S,4S enantiomer.
[c]Average of two or more experiments.
[d]Compound tested as a mixture of A and B isomers (A:B, 2.3:1).

The affinity of the formula I compounds for the NMDA glutamate receptors was demonstrated by displacement of [$^3$H]CGS19755 binding to synaptosomal rat forebrain membranes. Murphy, et al., *British J. Pharmacol.*, 95, 932–938 (1988). Generally, the formula I compounds produced a measurable displacement of [$^3$H]CGS19755 when tested at 100 mM.

The compounds of the present invention are preferably formulated prior to administration. Therefore, another aspect of the present invention is a pharmaceutical formulation comprising a compound of formula I in combination with one or more pharmaceutically-acceptable carriers, diluents, or excipients. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantity (mg/capsule) |
| --- | --- |
| 4-(4-Methylphenoxy)glutamic Acid | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
| --- | --- |
| 4-(4-(1-Phenylhexyl)phenoxy) glutamic Acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| 4-(4-(1-(4-Nitrophenyl)ethenyl) phenoxy)glutamic Acid | 0.25 |
| Ethanol | 29.75 |
| Propellant 22 | 70.00 |
| (chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| 4-(5,6,7,8-Tetrahydro-2- dibenzofuranoxy)glutamic Acid | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules each containing 80 mg medicament are made as follows:

| 4-(4-(1-Phenylprop-1-enyl)phenoxy) glutamic Acid | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| 4-(2-Naphthyloxy)glutamic Acid | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| 4-(6-Bromo-2-naphthyloxy)glutamic Acid | 50 mg |
| --- | --- |
| Sodium carboxymethyl cellulose | 50 mg |
| Syrup | 1.25 ml |
| Benzoic acid solution | 0.10 ml |

| Flavor | q.v. |
| --- | --- |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| 4-(2-Fluorenoxy)glutamic Acid | 100 mg |
| --- | --- |
| Mannitol | 100 mg |
| 5N Sodium hydroxide | 200 ml |
| Purified water to total | 5 ml |

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. Dry tetrahydrofuran (THF) was obtained by distillation from sodium or sodium benzophenone ketyl prior to use. All other solvents and reagents were used as obtained. Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz, using $d_6$-DMSO as the solvent unless stated otherwise. Free atom bombardment mass spectroscopy (FABMS) was performed on a VG ZAB-2SE instrument. Field desorption mass spectroscopy (FDMS) was performed using either a VG 70SE or a Varian MAT 731 instrument. Optical rotations were measured with a Perkin-Elmer 241 polarimeter. Chromatographic separation on a Waters Prep 500 LC was generally carried out using a linear gradient of the solvents indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography was performed as described by Still, et al. Still, Kahn, and Mitra, *J. Org. Chem.*, 43, 2923 (1978). Elemental analyses for carbon, hydrogen and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Gallenkamp hot air bath melting point apparatus or a Büchi melting point apparatus, and are uncorrected. The number in parenthesis after the compound name refers to either the compound number or a general formula.

EXAMPLE 1

Preparation of N-Benzyloxycarbonyl-2-oxa-3-azabicyclo [2.2.1]hept-5-ene (V)

Cyclopentadiene was distilled from dicyclopentadiene using a Vigreux column (8 cm), collecting the distillate (boiling point 42° C.) in a cooled receiver (dry ice/acetone).

Methylene chloride (1000 ml) was stirred in an ice/acetone bath, and treated with freshly distilled cyclopentadiene (59.6 g) and benzyl N-hydroxycarbamate (166.5 g). The resulting solution was treated with a suspension of tetrabutylammonium periodate (429 g) in methylene chloride (900 ml) at a rate such that the temperature remained below 3° C. After the addition of the periodate suspension was complete (ca. 20 min.), the resulting reaction mixture was stirred at −5° C. for 2 hours. The ice/acetone bath was replaced with a dry ice/acetone bath, that was kept at a temperature of about −25° C. to about −30° C. by the addition of dry ice. A solution of sodium bisulfite (340.5 g) in water (1350 ml) was added at a rate such that the temperature of the reaction mixture was between about −2° C. and about 6° C. After about 50 minutes, the addition of the sodium bisulfite solution was complete. The organic phase was removed, and water (1050 ml) was added to the aqueous phase, causing further separation of the organic and aqueous phases. The combined organic phases were washed with water 3×1600 ml) and saturated sodium bicarbonate solution (1050 ml), water (1600 ml), and 1N hydrochloric acid (1200 ml). The organic phase was dried over sodium chloride and magnesium sulfate, filtered, and concentrated in vacuo to give 547.5 g of a brown solid. This solid was treated with diethyl ether (1400 ml) and the resulting mixture filtered. The lilt rate was evaporated to a solid (206.0 g). A solution of this solid in methylene chloride was added to silica gel (412 g), and the resulting mixture evaporated to dryness. The title compound was isolated by flash silica-gel filtration, eluting with hexane/ethyl acetate (4:1, 4×3 L) followed by hexane/ethyl acetate (2:1, 6×3 L). The fractions containing the title compound were combined and concentrated in vacuo to give a golden yellow oil. This oil was seeded with a solid sample of the title compound, to give 194.9 g of the title compound as a solid.

Mass spectrum (FDMS): m/z=231 (M$^+$).

$^1$H NMR (CDCl$_3$): d 7.31 (5H), 5.17 (4H), 2.01 (d, 1H), 1.75 (d, 1H).

Analysis calculated for C$_{13}$H$_{13}$NO$_3$: C, 67.52; H, 5.67; N, 6.06. Found: C, 67.25; H, 5.69; N, 5.96.

EXAMPLE 2

N-Benzyloxycarbonyl-3,5-dicarboxy-1,2-oxazoline (VI)

A potassium permanganate solution was prepared by stirring potassium permanganate (123.2 g) in water (800 ml) at 55° C. After stirring overnight, the liquid was decanted. The residue was partially dissolved in water (100 ml) at 55° C. The solids were separated from the solution by decanting, and washed with water (50 ml). These solutions were combined for use below.

A two-phase mixture of the compound prepared as described in Example 1 (69.4 g) in toluene (694 ml) and water (150 ml) was treated with tetrabutylammonium hydrogen sulfate (10.2 g). The resulting mixture was stirred with a mechanical stirrer, cooled by partial immersion in an acetone/dry ice bath to a temperature of about 2° C., and treated with the potassium permanganate solution at a rate such that the temperature was below 6° C. Care must be taken, especially at the beginning of the reaction, to ensure that the aqueous phase does not freeze. After 50 minutes, the addition of the potassium permanganate solution was complete. The resulting slurry was mechanically stirred for 2.2 hours in an ice/water bath. The reaction mixture was treated with Celite (348 g) and filtered through a dry Celite bed, with pressing to prevent channeling. The solids were washed with methanol/water (3600 ml, 4:1). The filtrate was concentrated in vacuo to a volume of about 400 ml. This concentrate was treated with water (100 ml) and ethyl acetate (600 ml). The pH of this mixture was adjusted to pH 0.81 by the addition of 18N sulfuric acid (110 ml). The phases were separated and the aqueous phase extracted with ethyl acetate (500 ml, 400 ml). The combined organics were dried over sodium chloride and magnesium sulfate, filtered, and concentrated in vacuo. This material, which was about 85% pure, was used in the next reaction without further purification.

$^1$H NMR: d 7.31 (5H), 5.11 (2H), 4.71 (q, 1H), 4.55 (t, 1H), 2.88 (m, 1H), 2.38 (m, 1H).

EXAMPLE 3

N-Benzyloxycarbonyl-3,5-dimethoxycarbonyl-1,2-oxazoline (VII)

A solution of the crude compound prepared as described in Example 2 (79.5 g) in methylene chloride (1000 ml) was cooled to a temperature of about −40° C. in an acetonitrile/dry ice bath. This cold solution was treated with N,N-diisopropylethylamine (68.7 g) over a five minute period. The cold solution was then treated with trimethyloxonium tetrafluoroborate (78.5 g). The temperature of the reaction was kept below −37° C. by cooling with the acetonitrile/dry ice bath. After about three hours, the reaction mixture was allowed to warm to −25° C. for one hour, then the cooling bath was removed. The reaction mixture was treated with water (500 ml) and the phases separated. The organic phase was washed with sodium bisulfate solution (2×400 ml, 1×200 ml). The organic phase was dried over sodium chloride, filtered, and concentrated in vacuo to give 81.18 g. The residue was dissolved in methylene chloride (600 ml), and treated with silica-gel (153 g). This mixture was concentrated in vacuo to a powder and subjected to flash filtration. The title compound was eluted with hexane/ethyl acetate (4:1, 8 L) followed by hexane/ethyl acetate (2:1, 19 L). The fractions containing the title compound were combined and concentrated in vacuo to give 49.4 g of a yellow orange oil.

Mass spectrum (FDMS): m/z=323 (M$^+$).

$^1$H NMR: d 7.31 (5H), 5.12 (s,2H), 4.87 (q, 1H), 4.71 (t, 1H), 3.63 (d, 6H), 2.91 (m, 1H), 2.51 (m, 1H).

Analysis calculated for C$_{15}$H$_{17}$NO$_7$: C, 55.73; H, 5.30; N, 4.33. Found: C, 55.63; H, 5.34; N, 4.38.

EXAMPLE 4

Methyl 3-Hydroxy-2-pyrrolidone-5-carboxylate (IV)

A mixture of the compound prepared as described in Example 3 (73.1 g) and 10% palladium on carbon (20.0 g) in tetrahydrofuran (600 ml) was hydrogenated at a hydrogen pressure of 48 psi and at room temperature. After 18 hours, the reaction was filtered and the filtrate was concentrated in vacuo. Analysis of the crude product (TLC) indicated the reduction was not complete. The crude product was mixed with 10% palladium on carbon (6.0 g) and tetrahydrofuran (430 mL), and hydrogenated at room temperature. After 18 hours, the reaction was filtered and the filtrate concentrated in vacuo. The residue was dissolved in a small volume of ethyl acetate and treated with silica-gel (150 g). The resulting mixture was subjected to flash chromatography, was eluting with a gradient of 10% hexane/ethyl acetate to 10% methanol/ethyl acetate. The fractions containing the title compound were combined and concentrated in vacuo to give a brown oil. This oil was dissolved in acetone (90 ml), and the resulting solution was concentrated in vacuo. The residue was diluted with ethyl acetate (25 ml), resulting in immediate crystal formation. Additional ethyl acetate (25 ml) was added to the mixture. The crystalline material was collected by filtration and washed with ethyl acetate (50 ml). This material was dried in vacuo to give 11.54 g of the title compound. The filtrate was concentrated in vacuo until a second crop of crystals began to form. These crystals were collected by filtration, washed with ethyl acetate (10 ml), and dried in vacuo to give 2.54 g of the title compound.

Melting point 85°–86° C.

Mass spectrum (FDMS): m/z=160 (M$^+$).

$^1$H NMR: d 8.11 (s, 1H), 5.52 (s, 1H), 4.11 (dd, 1H), 4.0 (q, 1H), 3.62 (s, 3H), 2.29 (m, 1H), 2.01 (m, 1H).

Analysis calculated for C$_6$H$_9$NO$_4$: C, 45.28; H, 5.70; N, 8.80. Found: C, 45,54; H, 5.70; N, 8.54.

EXAMPLE 5

Methyl 3-(2-Methylphenoxy)-2-pyrrolidone-5-carboxylate (VIII)

A mixture of the compound prepared as described in Example 4 (0.695 g), triphenylphosphine (1.259 g), and o-cresol (0.519 g) in tetrahydrofuran (6.3 ml) was cooled to 5° C., and treated with a solution of diethyl azodicarboxylate (0.863 g) in tetrahydrofuran (1.8 ml) over a six minute period. After the addition was complete, the reaction was allowed to warm to room temperature. After about 18 hours, the reaction solution was concentrated in vacuo. The residue was diluted with chloroform, the insoluble material removed by filtration, and the filtrate concentrated in vacuo. The residue was dissolved in a small volume of methylene chloride (4 ml) and purified by preparative centrifugal thin-layer chromatography, eluting with 50% ethyl acetate/hexane followed by 75% ethyl acetate/hexane. The fractions containing the title compound were combined and concentrated in vacuo to give 905 mg. This material contains triphenylphosphine oxide as an impurity.

Mass spectrum (FDMS): m/z=249.

$^1$H NMR: d 7.12 (2H), 7.05 (1H), 6.83 (t,1H), 4.84 (1H), 4.24 (1H), 3.66 (s,3H), 2.88 (m, 1H), 2.08 (s,3H), 1.99 (1H).

EXAMPLE 6

4-(2-Methylphenoxy)glutamic acid (4)

A mixture of lithium hydroxide (0.0939 g) in water (1.5 ml) and tetrahydrofuran (4.3 ml) was treated with the compound prepared as described in Example 5 (0.326 g), and heated to about 62° C. After about 2¾ hours, the reaction mixture was allowed to cool to room temperature. After an additional 2 hours, the reaction mixture was treated with 5N hydrochloric acid (784 ml). The resulting solution was concentrated in vacuo to give an oily solid. This material was treated with tetrahydrofuran/water (1:1, 10 ml) and the resulting insoluble material collected by filtration. The solids were washed sequentially with tetrahydrofuran/water (1:1, 2 ml), water (3 ml), and tetrahydrofuran (10 ml). This material was dried in vacuo at 60° C. for about 18 hours to give 84 mg of the title compound.

Mass spectrum (FABMS): m/z=254.

$^1$H NMR: d 7.09 (2H), 6.81 (1H), 6.57 (1H), 4.77 (t,1H), 3.66 (t,1H), 2.19 (m,5H).

EXAMPLE 7

Methyl 3-(2-Naphthalenethio)-2-pyrrolidone-5-carboxylate (VIII)

A solution of the compound prepared as described in Example 4 (0.553 g), triphenylphosphine (1.02 g), and 2-naphthalenethiol (0.474 g) in tetrahydrofuran (4.9 ml) was cooled to 0° C. This cold solution was treated with a solution of diethyl azodicarboxylate (0.665 g) in tetrahydrofuran (1.4 ml) over a one minute period. After the addition was complete, the reaction was allowed to warm to room temperature. After about 23 hours, the reaction solution was concentrated in vacuo. The residue was diluted with methylene chloride. The insoluble material was removed by filtration and washed with methylene chloride (2 ml), and the filtrate concentrated in vacuo. This residue was dissolved in small volume of ethyl acetate and purified by preparative centrifugal thin-layer chromatography, eluting with 50% ethyl acetate/hexane followed by 75% ethyl acetate/hexane. The fractions containing the title compound were combined and concentrated in vacuo to give 416 mg. This material contains triphenylphosphine oxide as an impurity.

Mass spectrum (FDMS): m/z=301.

EXAMPLE 8

4-(2-Naphthalenethio)glutamic Acid (24A and 24B)

A mixture of the compound prepared as described in Example 7 (1.53 g) in tetrahydrofuran (14.5 ml) and water (5.1 ml) was treated with lithium hydroxide (0.365 g) and heated to about 60° C. After about 3⅓ hours, the reaction mixture was allowed to cool to room temperature. After an additional hour, the reaction mixture was treated with 5N hydrochloric acid (3.04 ml). The resulting solution was placed in a freezer overnight. This solution was partially concentrated in vacuo to remove the tetrahydrofuran, and the residue extracted with methylene chloride (3×20 ml). The aqueous phase was applied to a cation-exchange chromatography column (DOWEX 50 X-8). The column was washed sequentially with water (200 ml), 50% tetrahydrofuran/water (200 ml), and water (200 ml). The title compound was eluted using 10% pyridine/water. The fractions containing the title compound were combined and concentrated in vacuo to a volume of about 70 ml to induce crystallization. The crystalline material was collected by filtration, washed with water, and dried at room temperature under vacuum over $P_2O_5$ to give 307 mg of a mixture of diastereomers (A/B=2.3:1). The filtrate was concentrate in vacuo to a volume of about 53 ml which resulted in additional crystal formation. These crystals were removed by filtration and washed with water. This filtrate was concentrated in vacuo to dryness to give 250 mg of a mixture of diastereomers (B/A=2.3:1).

Compound 24A $^1$H NMR: d 7.83 (m,3H), 7.51 (m, 4H), 4.34 (t,1H), 3.50 (t, 1H), 2.22 (m, 1H), 1.91 (m, 1H).

Analysis calculated for $C_{15}H_{15}NO_4S$: C, 59.00; H, 4.95; N, 4.59; S, 10.50. Found: C, 59.19; H, 4.83; N, 4.38; S, 10.30.

Compound 24B

Mass spectrum (FABMS): m/z=306 (M+1).

$^1$H NMR: d 7.83 (m,3H), 7.47 (m, 4H), 4.23 (m, 1H), 3.58 (1H), 2.01 (m, 2H).

EXAMPLE 9

4-Phenoxyglutamic Acid (1)

The title compound was prepared substantially as described in Examples 5 and 6, except using phenol.

Mass spectrum (FABMS): m/z=240 (M+1), 221 (M—$H_2O$), 195 (M—$CO_2$).

$^1$H NMR: d 7.22 (t,2H), 6.88 (t,1H), 6.74 (d,2H), 4.75 (t, 1H), 3.63 (t, 1H), 2.22–2.08 (m, 2H).

Analysis calculated for $C_{11}H_{13}NO_5$: C, 55.23; H, 5.48; N, 5.86. Found: C, 55.23; H, 5.27; N, 5.72.

EXAMPLE 10

4-Benzenethioglutamic Acid (2)

The title compound was prepared substantially as described in Examples 5 and 6, except using thiophenol.

Mass spectrum (FABMS): m/z=256 (M+1), 237 (M—$H_2O$).

$^1$H NMR: d 7.42 (d, 2H), 7.27 (m, 3H), 4.21 (t, 1H), 3.43 (1H), 2.16 (m, 1H), 1.84 (m, 1H).

EXAMPLE 11

4-(4-Methylphenoxy)glutamic Acid (3)

The title compound was prepared substantially as described in Examples 5 and 6, except using p-cresol. The title compound was purified by cation-exchange chromatography (DOWEX 50X-8), eluting with 10% pyridine/water.

Mass spectrum (FABMS): m/z=254 (M+1), 235 (M—$H_2O$), (M+1—$CO_2$).

$^1$H NMR: d 7.00 (d,2H), 6.72 (d, 2H), 4.89 (q, 1H), 3.96 (m, 1H), 2.14 (s,3H), 2.34 (t,2H).

EXAMPLE 12

4-(4 Methoxyphenoxy)glutamic Acid (5)

The title compound was prepared substantially as described in Examples 5 and 6, except using 4-methoxyphenol.

Mass spectrum (FABMS): m/z=270 (M+1).

$^1$H NMR: d 6.77 (m, 4H), 4.68 (t, 1H), 3.62 (m, 4H), 2.15 (m,2H).

Analysis calculated for $C_{12}H_{15}NO_6$: C, 53.53; H, 5.62; N, 5.20. Found: C, 53.26; H, 5.55; N, 4.98.

EXAMPLE 13

4-(4-(Isopropyl)phenoxy)glutamic Acid (6)

The title compound was prepared substantially as described in Examples 5 and 6, except using 4-isopropylphenol.

Mass spectrum (FABMS): m/z=282 (M+1).

$^1$H NMR: d 7.09 (d,2H), 6.67 (d, 2H), 4.71 (1H), 3.61 (1H), 2.76 (1H), 2.23–2.07 (m,2H), 1.12 (d,6H).

Analysis calculated for $C_{14}H_{19}NO_5$: C, 59.78; H, 6.81; N, 4.98. Found: C, 59.17; H, 6.69; N, 4.84.

EXAMPLE 14

4-(4-Cyclopentylphenoxy)glutamic Acid (7)

The title compound was prepared substantially as described in Examples 5 and 6, except using 4-cyclopentylphenol.

Mass spectrum (FABMS): m/z=308 (M+1), 217 (M—$CO_2$).

$^1$H NMR: d 7.10 (d,2H), 6.68 (d,2H), 4.73 (t,1H), 3.63 (t,1H), 2.84 (1H), 2.18 (m,2H), 1.93 (2H), 1.57 (6H).

Analysis calculated for $C_{16}H_{21}NO_5$: C, 62.53; H, 6.89; N, 4.56. Found: C, 62.61; H, 6.89; N, 4.60.

EXAMPLE 15

4-(4-(1,1,3,3-Tetramethylbutyl)phenoxy)glutamic Acid (8)

The title compound was prepared substantially as described in Examples 5 and 6, except using 4-(t-octyl)phenol. The title compound was purified using cation-exchange chromatography (DOWEX 50X-8), eluting with 10% pyridine/water.

Mass spectrum (FABMS): m/z=352 (M+1), 308 (M+H—CO$_2$).

$^1$H NMR: d 7.24 (d,2H), 6.67 (d,2H), 4.72 (1H), 3.63 (1H), 2.23–2.06 (brm, 2H), 1.65 (2H), 1.26 (s, 6H), 0.65 (s, 9H).

Analysis calculated for C$_{19}$H$_{29}$NO$_5$: C, 64.94; H, 8.32; N, 3.99. Found: C, 65.12; H, 8.47; N. 3.82.

EXAMPLE 16

4-(4-Acetylphenoxyl))glutamic Acid (9)

The title compound was prepared substantially as described in Examples 5 and 6, except using 4-hydroxyacetophenone.

Mass spectrum (FABMS): m/z=282 (M+1).

$^1$H NMR (d$_7$-DMF): d 8.08 (d, 2H), 6.93 (d,2H), 5.06 (t, 1H), 4.12 (t, 1H), 2.53 (s, 3H), 2.49 (m,2H).

EXAMPLE 17

4-(4-Trifluoromethylphenoxy)glutamic Acid (10)

The title compound was prepared substantially as described in Examples 5 and 6, except using 4-trifluouromethylphenol.

Mass spectrum (FABMS): m/z=308 (M+1).

$^1$H NMR: d 7.59 (d, 2H), 6.93 (d, 2H), 4.87 (t, 1H), 3.70 (t, 1H), 2.21 (bm, 2H).

Analysis calculated for C$_{12}$H$_{12}$NO$_5$: C, 46.91; H, 3.94; N, 4.56. Found: C, 47.12; H, 3.93; N, 4.49.

EXAMPLE 18

4-(3,4-Dichlorophenoxy)glutamic Acid (11)

The title compound was prepared substantially as described in Examples 5 and 6, except using 3,4-dichlorophenol.

Mass spectrum (FABMS): m/z=308 (M).

$^1$H NMR: d 7.45 (d, 1H), 7.05 (d, 1H), 6.80 (dd, 1H), 4.81 (t, 1H), 3.69 (t, 1H), 2.21 (m, 2H).

Analysis calculated for C$_{11}$H$_{11}$NO$_5$: C, 42.88; H, 3.60; N, 4.55. Found: C, 42.36; H, 3.67; N, 4.35.

EXAMPLE 19

4-(4-Phenylphenoxy)glutamic Acid (12)

The title compound was prepared substantially as described in Examples 5 and 6, except using 4-phenylphenol.

Mass spectrum (FABMS): m/z=316 (M+1).

$^1$H NMR: d 7.55 (4H), 7.40 (t,2H), 7.28 (t,1H), 6.86 (d,2H), 4.83 (1H), 3.67 (1H), 2.30–2.16 (m,2H).

Analysis calculated for C$_{17}$H$_{17}$NO$_5$: C, 64.76; H, 5.43; N, 4.44. Found: C, 65.01; H, 5.44; N, 4.34.

EXAMPLE 20

4-(3-Phenylphenoxy)glutamic Acid (13)

The title compound was prepared substantially as described in Examples 5 and 6, except using 3-phenylphenol.

Mass spectrum (FABMS): m/z=316 (M+1).

$^1$H NMR: d 7.55 (2H), 7.42 (t,2H), 7.31 (t,2H), 7.18 (d, 1H), 7.02 (s,1H), 6.84 (d, 1H), 6.75 (dd, 1H), 4.86 (t, 1H), 3.65 (t, 1H), 2.32–2.10 (m, 2H).

Analysis calculated for C$_{17}$H$_{17}$NO$_5$: C, 64.75; H, 5.43; N, 4.44. Found: C, 64.79; H, 5.41; N, 4.43.

EXAMPLE 21

4-(4-Benzylphenoxy)glutamic Acid (14)

The title compound was prepared substantially as described in Examples 5 and 6, except using 4-hydroxydiphenylmethane.

Mass spectrum (FABMS): m/z=330 (M+1).

$^1$H NMR: d 7.26–7.07 (7H), 6.69 (d,2H), 4.72 (t,1H), 3.62 (1H), 2.27–2.06 (m, 2H).

EXAMPLE 22

4-(2-Benzylphenoxy)glutamic Acid (15)

The title compound was prepared substantially as described in Examples 5 and 6, except using 2-hydroxydiphenylmethane.

Mass spectrum (FABMS): m/z=330 (M+1), 311 (M-H$_2$O).

$^1$H NMR: d 7.21 (4H), 7.10 (3H), 6.81 (t,1H), 6.60 (d, 1H), 4.78 (t, 1H), 3.89 (q, 2H), 3.63 (t, 1H), 2.28–2.15 (m, 2H).

Analysis calculated for C$_{18}$H$_{19}$NO$_5$: C, 65.64; H, 5.81; N, 4.25; Found: C, 65.40; H, 5.69; N, 4.05.

EXAMPLE 23

4-(4-(6-Phenylhexyl)phenoxy)glutamic Acid (16)

(i) A mixture of 1,4-dibenzoylbutane (119 g) and 5% palladium on carbon (15.0 g) in ethyl acetate (1.335 L) and concentrated sulfuric acid (11.3 ml) was hydrogenated at a hydrogen pressure of 60 psi and at 50° C. After 3 hours, the reaction was allowed to cool to room temperature. The reaction mixture was treated with water (2×500 ml) and the phases separated. The organic phase was washed with 10% aqueous sodium bicarbonate solution (250 ml). The organic phase was dried over sodium chloride, filtered, and concentrated in vacuo to give an oil. The oil was subjected to vacuum distillation. Distillation at 141°–151° C., 0.24 mm Mercury gave 119 g of 1,6-diphenylhexane as a colorless oil.

$^1$H NMR: d 7.26–7.21 (4H), 7.15–7.11 (6H), 2.52 (t,3H), 1.54–1.48 (4H), 1.30–1.26 (4H).

(ii) A solution of 1,6-diphenylhexane (119.05 g) and acetic anhydride (50.98 g) in 1,1,2,2-tetrachloroethane (375 ml) was cooled to a temperature of about −38° C. in an acetone/dry ice bath. To the solution was added aluminum chloride at a rate such that the temperature remained below −19° C. After the addition of the aluminum chloride was complete (ca. 80 min.), the resulting reaction suspension was allowed to warm to room temperature. After approximately 1.7 hours at room temperature, the reaction was cooled to approximately 0° C. in an water/ice bath, then treated with 6N HCl (150 ml) at a rate such that the temperature remained below 8° C. The reaction was treated with water (500 ml) and the phases separated. The aqueous layer was treated with chloroform (3×250 ml) and the phases were separated. The combined organic phases were washed with water (250 ml), dried over sodium chloride, filtered and concentrated in vacuo to give an oil that solidified upon standing at room temperature. A solution of this solid in methylene chloride was subjected to vacuum distillation at 200°–210° C., 0.1 mm Mercury to give 4'-(6-phenylhexyl)acetophenone, 61.45 g, as an oil.

$^1$H NMR: d 7.84 (d,2H), 7.30 (d,2H), 7.26–7.21 (2H), 7.15–7.10 (3H), 2.60 (t, 2H), 2.52 (5H), 1.56–1.50 (4H), 1.29 (4H).

(iii) A biphasic solution of 4'-(6-phenylhexyl) acetophenone (61.36 g) and m-chloroperbenzoic acid (166.15 g) in methylene chloride (550 ml) was refluxed. (Note: the m-chloroperbenzoic acid used in this reaction was a mixture of 1:1 m-chloroperbenzoic acid and m-chlorobenzoic acid.) After 22 hours, the reaction was allowed to cool to room temperature. The reaction mixture was filtered and the insolubles washed with methylene chloride (50 ml). To the filtrate was added water (250 ml). The pH of the biphasic solution was adjusted from 3.3.4 to 5.98 with 5N NaOH (14 ml). To the biphasic solution was added additional water (250 ml) and the phases were separated. The organic phase was treated with 10% aqueous potassium carbonate (2×250 ml) then with brine (3×500 ml). The organic phase was dried over sodium chloride then magnesium sulfate, filtered, concentrated in vacuo to give a semi crystalline solid.

After approximately 15 minutes at room temperature, the isolated material exothermed. Approximately ten minutes later, a brown oil was present. A solution of the oil in methylene chloride (1 L) was washed with saturated aqueous sodium bicarbonate (3×500 ml). The organic phase was dried over magnesium sulfate, filtered, concentrated in vacuo to afford 48.46 g of 4-(6-phenylhexyl)phenyl acetate as an oil.

(iv) To a mixture of 4-(6-phenylhexyl) phenyl acetate in methanol (620 ml) and water (550 ml) was added sodium carbonate (71.86 g). The resulting suspension was refluxed. After 2.5 hours, the reaction was allowed to cool to room temperature. After 1.5 hours, the reaction was concentrated in vacuo to remove the majority of methanol present. Additional water (600 ml) was added to the reaction mixture. The reaction mixture was then treated with diethyl ether (4×500 ml). The combined organic phases were washed with 1N HCl (3×100 ml), dried over magnesium sulfate, then filtered. To the filtrate was added 230–400 mesh silica-gel (70 g), and the resulting mixture evaporated to dryness. The desired compound was isolated by flash silica-gel chromatography, eluting with hexane/ethyl acetate (1:0.00125, 1×500 ml, 6×250 ml) then hexane/ethyl acetate (1:0.05, 4×250 ml) followed by hexane/ethyl acetate (1:0.1, 4×250) and finally hexane/ethyl acetate (1:0.15, 4×250 ml). The fractions containing 1-(4-hydroxyphenyl)-6-phenylhexane were combined and concentrated in vacuo to give 20.42 g of an oil. Upon standing at room temperature the oil crystallized out.

Mass spectrum (FDMS): m/z 254

$^1$H NMR: d 9.06 (1H), 7.23 (2H), 7.13 (3H), 6.92 (2H), 6.61 (2H), 2.51 (t,2H), 2.40 (t,2H), 1.56–1.41 (4H), 1.31–1.24 (4H).

(v) A mixture of the compound prepared as described in Example 4 (3.612 g), triphenylphosphine (6.759 g), and 1-(4-hydroxyphenyl)-6-phenylhexane (6.555 g) in tetrahydrofuran (32 ml) was cooled to approximately 1°–2° C., and treated with a solution of diethylazodicarboxylate (4.080 g) in tetrahydrofuran (10 ml) over a seventeen minute period. After the addition was complete, the reaction suspension was allowed to warm to room temperature. After about 24 hours, the resulting brown solution was concentrated in vacuo. The residue was diluted with chloroform (10 ml), the insoluble material removed by filtration, and the filtrate concentrated in vacuo. The material was dissolved in methylene chloride and 230–400 mesh silica gel (36 g) was added. The mixture was concentrated in vacuo to a powder. The mixture was subjected to flash silica gel chromatography, eluting with hexane/ethyl acetate (5:2, 10×100 ml), then hexane/ethyl acetate (5:3, 7×100 ml, 1×200 ml), next ethyl ether (10×200 ml) and finally ethyl acetate (2×200 ml, 2×500 ml). The fractions containing the desired material were concentrated in vacuo to give a gold oil. The gold oil was dissolved in methylene chloride (24 ml) and purified by preparative centrifugal thin-layer chromatography (4mm plate, flow rate=8 ml/min), eluting with 50% ethyl acetate/hexane until the first band elutes then solvent switched to ethyl acetate. The fractions containing methyl 3-[4-(6-hexylphenyl)phenoxy]-2-pyrrolidone-5-carboxylate were combined and concentrated in vacuo to give a gold oil. The oil was dissolved in diethyl ether (10 ml). Hexane was added until the solution became turbid. After forty five minutes at room temperature, the turbid solution was concentrated in vacuo resulting in the formation of a solid material. Diethyl ether (10 ml) was added to the material, then the insolubles were collected by filtration. The filtrate was concentrated in vacuo to give an oil that crystallizes out. Diethyl ether was added to the crystalline material. The resulting suspension was rigorously stirred for thirty minutes. Insolubles were collected by filtration to give 3.91 g of methyl 3-(4-(6-hexylphenyl)phenoxy]-2-pyrrolidone-5-carboxylate.

$^1$H NMR: d 8.54 (1H), 7.23 (2H), 7.13 (3H), 7.04 (2H), 6.85 (2H), 4.83 (1H), 4.21 (t, 1H), 2.89 (m, 1H), 2.54–2.37 (4H), 1.88 (m, 1H), 1.56–1.44 (4H), 1.29–1.14 (4H).

(vi) A mixture of lithium hydroxide (0.712 g) in water (9.3 ml) and tetrahydrofuran (29 ml) was treated with methyl 3-[4-(6-hexylphenyl)phenoxy]-2-pyrrolidone-5-carboxylate (3.91 g), and heated to 58° C. After about 3.8 hours, the reaction mixture was allowed to cool to room temperature. The reaction mixture was then treated with 5N HCl (5.94 ml). The resulting light suspension was sonicated then stirred at room temperature for fifteen minutes. Insolubles were collected by filtration, washed with 1:1 tetrahydrofuran:water (10 ml), then tetrahydrofuran (10 ml) and finally water (10 ml). The title compound crystallized out from the filtrate and was collected by filtration. This material was dried in vacuo to give 1.077 g of the title compound.

Analysis calculated for $C_{23}H_{29}NO_5$: C, 69.15; H,7.32; N, 3.51; Found: C, 69.32; H, 7.29; N, 3.30

Mass spectrum (FABMS): m/z=400 (M+1), 382 (M+1-$H_2O$).

$^1$H NMR: d 7.22 (2H), 7.11 (3H), 7.02 (d,2H), 7.65 (d, 2H), 4.70 (q, 1H), 3.61 (q, 1H), 2.50 (1H), 2.14 (m, 2H), 1.47 (m,5H), 1.22 (m,5H).

EXAMPLE 24

4-(4-(3-Phenylprop-2-enyl)phenoxy)glutamic Acid (17)

The title compound was prepared substantially as described in Examples 5 and 6, except using 3-(4-hydroxyphenyl)-1-phenylprop-1-ene.

Mass spectrum (FABMS): m/z=356 (M+1).

$^1$H NMR: d 7.37 (2H), 7.27 (3H), 7.15 (2H), 6.72 (2H), 6.38 (2H), 4.74 (t, 1H), 3.63 (q, 1H), 3.42 (2H), 2.17 (m, 2H).

EXAMPLE 25

4-(4-(2-(4-Nitrophenyl)ethenyl)phenoxy)glutamic Acid (18)

The title compound was prepared substantially as described in Examples 5 and 6, except using 1-(4-hydroxyphenyl)-2-(4-nitrophenyl)ethene.

Mass spectrum (FABMS): m/z=387 (M+1), 341 (M+1-$NO_2$).

$^1$H NMR: d 8.19 (d, 2H), 7.80 (d, 2H), 7.58 (d, 2H), 7.23 (d,2H), 6.82 (d,2H), 4.84 (t,1H), 3.69 (1H), 2.21 (m,2H).

Analysis calculated for $C_{20}H_{21}NO_5$: C, 67.59; H,5.96; N,3.94; Found: C, 67.29; H, 5.89; N, 3.74.

EXAMPLE 26

4-(4-Phenoxyphenoxy)glutamic Acid (19)

The title compound was prepared substantially as described in Examples 5 and 6, except using 4-phenoxyphenol.

Mass spectrum (FABMS): m/z=331 (M), 313 (M-H$_2$O).

$^1$H NMR: d 7.29 (2H), 7.02 (1H), 6.96–6.74 (6H), 4.73 (t, 1H), 3.64 (t, 1H), 2.29–2.08 (m, 2H).

Analysis calculated for C$_{17}$N$_{17}$NO$_6$: C, 61.63; H, 5.17; N, 4.23. Found: C, 61.81; H, 5.12; N, 4.21.

EXAMPLE 27

4-(4-Benzyloxyphenoxy)glutamic Acid (20)

The title compound was prepared substantially as described in Examples 5 and 6, except using 4-benzyloxyphenol.

Mass spectrum (FABMS): m/z=346 (M+1), 256 (M+1-CO$_2$).

Analysis calculated for C$_{18}$H$_{19}$NO$_6$: C, 62.60; H, 5.45; N, 4.06. Found: C, 62.81; H, 5.67; N, 3.97.

EXAMPLE 28

4-(2-Naphthyloxy)glutamic Acid (21)

The title compound was prepared substantially as described in Examples 5 and 6, except using 2-naphthol.

Mass spectrum (FABMS): m/z=290 (M+1).

$^1$H NMR: d 7.76 (3H), 7.40 (t,1H), 7.30 (t,1H), 7.13 (dd, 1H), 7.01 (d, 1H), 4.94 (t, 1H), 2.40–2.15 (m, 2H).

Analysis calculated for C$_{15}$H$_{15}$NO$_5$: C, 62.28; H, 5.23; N, 4.84; Found: C, 61.98; H, 5.22; N, 4.66.

EXAMPLE 29

4-(6-Bromo-2-naphthyloxy)glutamic Acid (22)

(i) A mixture of the compound prepared as described in Example 4 (0.498 g), triphenylphosphine (0.932 g), and 6-bromo-2-naphthol (0.793 g) in tetrahydrofuran (4.3 ml) was cooled to approximately 1°–2° C., and treated with a solution of diethylazodicarboxylate (0.619 g) in tetrahydrofuran (4.3 ml) over a one minute period. After the addition was complete, the reaction was allowed to warm to room temperature. After about 23 hours, the solution was concentrated in vacuo. The residue was diluted with chloroform (2 ml), the insoluble material removed by filtration, and the filtrate concentrated in vacuo. The oil was dissolved in methylene chloride and purified by preparative centrifugal thin-layer chromatography (4 mm plate, flow rate=8 ml/min), eluting with ethyl acetate/hexane (1:1) until first band elutes then solvent switched to hexane:ethyl acetate (1:3). The fractions containing the title compound were combined, dried over magnesium sulfate, filtered and concentrated in vacuo to give methyl 3-(6-bromo-2-naphthyloxy)-2-pyrrolidone-5-carboxylate (778 mg).

Mass spectrum (FDMS): m/z 363,365

$^1$H NMR: d 8.63 (s, 1H), 8.09 (s, 1H), 7.81 (d, 1H), 7.73 (d, 1H), 7.61–7.45 (1H +O=PPh$_3$), 7.42 (1H), 7.21 (dd, 1H), 5.04 (t, 1H), 4.26 (t, 1H), 3.65 (s, 3H), 3.09–2.99 (m, 1H), 1.92–2.01 (m, 1H).

(ii) A mixture of lithium hydroxide (0.156 g) in water (2.0 ml) and tetrahydrofuran (6.6 ml) was treated with methyl 3-(6-bromo-2-naphthyloxy)-2-pyrrolidone-5-carboxylate (0.615 g), and heated to 60° C. After about 3.0 hours, the reaction mixture was allowed to cool to room temperature. The reaction mixture was treated with 5N HCl (1.30 ml). The insolubles were collected by filtration, washed with 1:1 THF:water (10 ml), THF (10 ml), and water (5 ml). The insolubles were dried overnight in at vacuum oven at 60° C. to afford the title compound.

Mass spectrum (FABMS): m/z=368,350 (M-H$_2$O).

$^1$H NMR: d 8.06 (s, 1H), 7.76 (2H), 7.50 (dd, 1H), 7.18 (dd, 1H), 7.05 (d, 1H), 4.94 (t,1H), 3.70 (1H), 2.30–1.70 (m,2H).

Analysis calculated for C$_{15}$H$_{14}$BrNO$_5$: C, 48.93; H, 3.83; N, 3.80. Found: C, 48.65; H, 3.81; N, 3.66.

EXAMPLE 30

4-(1,6-Dibromo-2-naphthyloxy)glutamic Acid (23)

The title compound was prepared substantially as described in Examples 5 and 6, except using 1,6-dibromo-2-naphthol.

Mass spectrum (FABMS): 447,368 (M-Br).

$^1$H NMR: d 8.17 (1H), 7.99 (d, 1H), 7.89 (d,1H), 7.70 (dd, 1H), 7.18 (d, 1H), 5.03 (t,1H), 3.78 (t,1H), 2.30 (m,2H).

Analysis calculated for C$_{15}$H$_{13}$BrNO$_5$: C, 40.30; H, 2.93; N, 3.14. Found: C, 40.35; H, 2.92; N, 3.11.

EXAMPLE 31

4-(1-Naphthyloxy)glutamic Acid (25)

The title compound was prepared substantially as described in Examples 5 and 6, except using 1-naphthol.

Mass spectrum (FABMS): m/z=290 (M+1).

$^1$H NMR: d 8.18 (1H), 7.85 (1H), 7.49 (3H), 7.35 (t,1H), 6.64 (d, 1H), 4.99 (t,1H), 3.75 (t,1H), 2.36 (m,2H).

Analysis calculated for C$_{15}$H$_{15}$NO$_5$: C, 62.28; H, 5.23; N, 4.84. Found: C, 62.49; H, 5.15; N, 4.80.

EXAMPLE 32

4-(5,6,7,8-Tetrahydro-1-naphthyloxy)glutamic Acid (26)

The title compound was prepared substantially as described in Examples 5 and 6, except using 5,6,7,8-tetrahydro-1-naphthol.

Mass spectrum (FABMS): m/z=294 (M+1), 250 (M+1-CO$_2$).

$^1$H NMR: d 6.95 (1H), 6.62 (d, 1H), 6.36 (d, 1H), 4.72 (1H), 3.64 (1H), 2.65–2.10 (brm, 6H), 1.67 (4H).

Analysis calculated for C$_{15}$H$_{19}$NO$_5$: C, 61.42; H, 6.53; N, 4.78. Found: C, 61.40; H, 6.43; N, 4.73.

EXAMPLE 33

4-(6,7-Dihydro-5,5,8,8-tetramethyl-2-naphthyloxy) glutamic Acid (27)

The title compound was prepared substantially as described in Examples 5 and 6, except using 6,7-dihydro-5,5,8,8-tetramethyl-2-naphthyloxy.

Mass spectrum (FABMS): m/z=350 (M+1).

$^1$H NMR: d 7.18 (d, 1H), 6.96 (1H), 6.50 (1H), 4.71 (1H), 3.61 (1H), 2.44–2.07 (brm, 2H), 1.57 (4H), 1.17 (12H).

Analysis calculated for C$_{19}$N$_{27}$NO$_5$: C, 65.31; H, 7.79; N, 4.01. Found: C, 65.47; H, 7.89; N, 3.95.

EXAMPLE 34

4 -(5-Indanyloxy)glutamic Acid (28)

The title compound was prepared substantially as described in Examples 5 and 6, except using 5-indanol.

Mass spectrum (FABMS): m/z=280 (M+H).

$^1$H NMR: d 7.06 (d, 1H), 6.63 (s,1H), 6.54 (dd, 1H), 4.71 (1H), 3.62 (1H), 2.75 (m,4H), 2.44–2.07 (m,2H), 1.96 (2H).

EXAMPLE 35

4-(3,4-Methylenedioxyphenoxy)glutamic Acid (29)

The title compound was prepared substantially as described in Examples 5 and 6, except using 3,4-(methylenedioxy)phenol.

$^1$H NMR: d 6.74 (d, 1H), 6.48 (d, 1H), 6.17 (dd, 1H), 5.90 (s, 2H), 4.64 (q, 1H), 3.59 (q, 1H), 2.20–2.04 (m, 2H).

EXAMPLE 36

4-(2-Fluorenoxy)glutamic Acid (30)

(i) A mixture of the compound prepared as described in Example 4 (0.462 g), triphenylphosphine (0.864 g), and 2-hydroxyfluorene (0.600 g) in tetrahydrofuran (4.2 ml) was cooled to approximately 1°–2° C., and treated with a solution of diethylazodicarboxylate (0.573 g) in tetrahydrofuran (1.7 ml) over a five minute period. After the addition was complete, the reaction was allowed to warm to room temperature. After about 24 hours, the resulting suspension was filtered, and the insolubles washed with tetrahydrofuran (5 ml) to give 0.526 g of methyl 3-(2-fluorenoxy)-2-pyrrolidone-5-carboxylate. This material was dried in a vacuum oven at 60° C. for approximately 24 hours.

Mass spectrum (FDMS): m/z 323.

$^1$H NMR: d 8.58(s,1H), 7.75(d,2H), 7.50(d,1H), 7.27(t, 1H), 7.18(2H), 6.97(d, 1H), 4.95(t,1H), 4.24(t,1H), 3.81 (s, 2H), 3.65 (s, 3H), 3.00–2.90 (m, 1H), 1.98–1.90 (m, 1H)

(ii) A mixture of lithium hydroxide (0.117 g) in water (1.5 ml) and tetrahydrofuran (4.7 ml) was treated with methyl 3-(2-fluorenoxy)-2-pyrrolidone-5-carboxylate (0.526 g), and heated to 60° C. After about 3.3 hours, the reaction mixture was allowed to cool to room temperature. The reaction mixture was treated with 5N HCl (976 ml). The resulting colloidal suspension was sonicated for ten minutes. The insolubles were collected by filtration, washed with 1:1 THF:water (10 ml), THF (10 ml), and water (10 ml). The insolubles were dried overnight in at vacuum oven at 60° C. to afford the title compound.

Mass spectrum (FABMS): m/z=328 (M+1).

$^1$H NMR: 7.73 (d, 2H), 7.48 (d, 1H), 7.29 (t,1H), 7.19 (t, 1H), 6.98 (s, 1H), 6.81 (dd, 1H), 4.83 (t,1H), 3.82 (s,1H), 3.67 (q, 1H), 2.22 (bm, 2H).

Analysis calculated for $C_{18}H_{17}NO_5$: C, 66.05; H, 5.24; N, 4.28. Found: C, 65.83; H, 5.30; N, 4.21.

EXAMPLE 37

4-(2-Dibenzofuranoxy)glutamic Acid (31)

(i) A mixture of the compound prepared as described in Example (0.800 triphenylphosphine (1.450 g), and 2 -hydroxydibenzofuran (1.019 g) in tetrahydrofuran (7.0 ml) was cooled to approximately 2° C., and treated with a solution of diethylazodicarboxylate (0.963 g) in tetrahydrofuran (2.0 ml) over a two minute period. After the addition was complete, the reaction was allowed to warm to room temperature. After about 15.5 hours, the solution was concentrated in vacuo. The residue was diluted with toluene (5 ml), the insoluble material removed by filtration, and the filtrate concentrated in vacuo. The oil was dissolved in ethyl acetate and purified by preparative centrifugal thin-layer chromatography (4 mm plate, flow rate=8 ml/min), eluting with ethyl acetate/hexane (1: 1) until first band elutes then solvent switched to hexane:ethyl acetate (1:3). The fractions containing the title compound were combined, dried over magnesium sulfate, filtered and concentrated in vacuo to give methyl 3-(2-dibenzofuranoxy)-2-pyrrolidone-5-carboxylate (427 mg). This material contains triphenylphosphine oxide as an impurity.

Mass spectrum (FDMS): m/z 325.

$^1$H NMR: d 8.60(s,1H), 8.07(d, 1H), 7.75(d, 1H), 7.64–7.45 (3H+O=PPh$_3$), 7.35 (t, 1H), 7.13 (dd, 1H), 4.97 (t, 1H), 4.26(t,1H), 3.65(s,3H), 3.05–2.95(m, 1H), 2.03–1.94(m, 1H).

(ii) A mixture of lithium hydroxide (0.0943 g) in water (1.4 ml) and tetrahydrofuran (4.3 ml) was treated with methyl 3-(2-dibenzofuranoxy)-2-pyrrolidone-5-carboxylate (0.427 g), and heated to 61° C. After about 2.4 hours, the reaction mixture was allowed to cool to room temperature. The reaction mixture was treated with 5N HCl (787 ml). The reaction mixture was then treated with water (3 ml). The insolubles were collected by filtration , washed with 1:1 tetrahydrofuran:water (2 ml), tetrahydrofuran (5 ml). The insolubles were dried overnight in at vacuum oven at 70° C. to afford the title compound.

Mass spectrum (FABMS): m/z=330 (M+1), 331 (M-H$_2$O).

$^1$H NMR: d 8.07 (d, 1H), 7.63–7.53 (2H), 7.46 (t,1H), 7.32 (t,1H), 7.00 (dd,1H), 4.91 (1H), 3.69 (1H), 2.35–2.14 (m,2H).

EXAMPLE 38

4-(5,6,7,8-Tetrahydro-2-dibenzofuranoxy)glutamic Acid (32)

The title compound was prepared substantially as described in Examples 5 and 6, except using 2-hydroxy-5, 6,7,8-tetrahydro dibenzofuran.

Mass spectrum (FABMS): m/z=334 (M+1), 289 (M+1-$CO_2$).

$^1$H NMR: d 7.32 (d, 1H), 6.79 (d, 1H), 6.71 (dd, 1H), 4.79 (1H), 3.64 (1H), 2.65 (2H), 2.51–1.70 (brm, 8H).

Analysis calculated for $C_{17}H_{19}NO_6$: C, 61.25; H, 5.74; N, 4.20. Found: C, 60.96; H, 5.73; N, 4.16.

EXAMPLE 39

4-(2-Methyl-5-benzofuranyloxy)glutamic Acid (33)

The title compound was prepared substantially as described in Examples 5 and 6, except using 5-hydroxy-2-methylbenzofuran.

Mass spectrum (FABMS): m/z=294 (M+1), 276 (M+1-$H_2O$), 249 (M+1-$CO_2$).

$^1$H NMR: d 7.31 (d, 1H), 6.83 (d, 1H), 6.70 (dd, 1H), 6.47 (s,1H), 4.75 (t,1H), 3.63 (1H), 2.36 (s,3H), 2.26–2.12 (m,2H).

Analysis calculated for $C_{14}H_{15}NO_6$: C, 57.34; H,5.15; N,4.78; Found: C,57.45; H, 5.10; N, 4.64.

EXAMPLE 40

4-(5-Benzothiophenyloxy)glutamic Acid (34)

The title compound was prepared substantially as described in Examples 5 and 6, except using 5-hydroxybenzothiophene.

Mass spectrum (FABMS): m/z=296 (M+1), 251 (M+1-$CO_2$).

$^1$H NMR: d 7.82 (d, 1H), 7.69 (d, 1H), 7.34 (d, 1H), 7.16 (d, 1H), 6.93 (dd, 1H), 4.84 (q, 1H), 3.65 (1H), 2.31–2.12 (m, 2H).

Analysis calculated for $C_{13}H_{13}NO_5S$: C, 52.87; H, 4.44; N, 4.74. Found: C, 51.38; H, 4.34; N, 4.70.

EXAMPLE 41

4-(4-(4-Chlorophenylpyridin-2-yl-methyl)phenoxyglutamic Acid (35)

The title compound was prepared substantially as described in Examples 5 and 6, except using pyridin-2-yl-4-hydroxy-4-chlorodiphenylmethane.

Mass spectrum (FABMS): m/z=441 (M+1), 423 (M+1-$H_2O$), (M+1-$CO_2$).

$^1$H NMR: d 8.48 (1H), 7.70 (1H), 7.35–6.66 (10H), 5.60 (1H), 4.73 (1H), 3.61 (1H), 2.47 (2H), 2.27–2.05 (m,2H).

EXAMPLE 42

4-(4-Benzyl-1,2,4-triazole-3-thio)glutamic Acid (36)

The title compound was prepared substantially as described in Examples 7 and 8, except using 4-benzyl-1,2,4-triazole-3-thiol.

Mass spectrum (FABMS): m/z=337 (M+1), 319 (M+1-$H_2O$).

$^1$H NMR: d 8.68 and 8.66 (1H), 7.32–7.26 (m, 1H), 5.19 and 5.16 (2H), 4.20 and 4.33 (1H), 3.71–3.63 (m, 1H), 2.4–2.0 (m,2H).

Analysis calculated for $C_{14}H_{16}N_4O_4S \cdot 0.5H_2O$: C, 48.69; H, 4.96; N, 16.22. Found: C, 48.88; H, 4.93; N, 16.37.

EXAMPLE 43

4-(1-Benzyl-1,2,4-triazole-3-thio)glutamic Acid (37)

The title compound was prepared substantially as described in Examples 7 and 8, except using 1-benzyl-1,2,4-triazole-3-thiol. Cation-exchange chromatography provided two mixtures of diastereomers, 37B (A/B=1:4) and 37A (A/B=2:1).

Mass spectrum (FABMS): m/z=337 (M+1), 319 (M+1-$H_2O$).

$^1$H NMR: d 8.63 and 8.61 (1H), 7.35–7.24 (m,5H), 5.33 and 5.31 (2H), 4.46 and 4.34 (1H), 3.66–3.57 (1H), 2.4–2.0 (m,2H).

Analysis calculated for $C_{14}H_{16}N_4O_4S$: C, 49.99; H, 4.79; N, 16.66, S, 9.53. Found: C, 49.91; H, 4.91; N, 16.47; S, 9.26.

EXAMPLE 44

4-(5-((2-Chlorophenyl)ethenyl)-1,2,4-triazole-3-thio)glutamic Acid (38)

The title compound was prepared substantially as described in Examples 7 and 8, except using 5-(2-chlorophenyl)ethenyl-1,2,4-triazole-3-thiol.

Mass spectrum (FABMS): m/z=397 (M+1).

$^1$H NMR: d 8.02 (1H), 7.87 (q, 1H), 7.50-7.23 (m, 4H), 4.30 and 4.13 (1H), 3.75 (m,1H), 3.63 and 3.61 (3H), 2.19 (m, 1H).

Analysis calculated for $C_{16}H_{17}N_4O_4S \cdot 2H_2O$: C, 44.40; H, 4.89; N, 12.94. Found: C, 44.15; H, 4.64; N, 12.67.

EXAMPLE 45

4-(2-(Pyrimidinethio)glutamic Acid (39)

The title compound is prepared substantially as described in Examples 7 and 8, except using 2-pyrimidinethiol.

Mass spectrum (FABMS): m/z=258 (M+1).

$^1$H NMR: d 8.59 and 8.58 (2H), 7.18 (1H), 4.60 (m, 1H), 3.70 and 3.56 (1H), 2.44–2.04 (bm,2H).

EXAMPLE 46

4-(1-Methyltetrazole-5-thio)glutamic Acid (40)

The title compound is prepared substantially as described in Examples 7 and 8, except using 1-methyltetrazol-5-thiol.

Mass spectrum (FABMS): m/z=262 (M+1).

$^1$H NMR: d 4.53 and 4.30 (1H), 3.93 and 3.89 (3H), 3.79 and 3.63 (1H), 2.16 (bm, 2H).

EXAMPLE 47

N-Methoxycarbonyl-2-oxa-3-aza-bicyclo[2.2.2]oct-5-ene (V)

A suspension of methyl N-hydroxycarbamate (17.81 g) in methylene chloride (350 ml) was cooled to about −13° C. (ice/acetone bath), and sequentially treated with 1,3-cyclohexadiene (14.24 g) and a suspension of tetrabutylammonium periodate (84.73 g) in methylene chloride (550 ml). The periodate suspension was added over a one hour period causing the temperature of the reaction to rise to a maximum of −5° C. After the addition of the periodate suspension was complete, the resulting reaction mixture was stirred at about −10° C. for three hours. A 10% sodium bisulfite solution (750 ml) was carefully added to the reaction mixture, while cooling in an ice/acetone bath. After about 45 minutes, the addition of the sodium bisulfite solution was complete. The organic phase was removed, washed with water (2×200 ml) and saturated sodium bicarbonate solution (2×500 ml). The organic phase was dried over sodium chloride, filtered, and concentrated in vacuo to give 180 g of the crude product. A solution of the crude product in methylene chloride was added to silica gel (200 g), and the resulting mixture evaporated to dryness. The title compound was isolated by flash silica-gel filtration, eluting with hexane/ethyl acetate (9:1, 2 L) and hexane/ethyl acetate (7:3, 500 ml). The fractions containing the title compound were combined, dried over sodium chloride and magnesium sulfate, filtered, and concentrated in vacuo to give 27.85 g of an oil. The oil was placed in a freezer to induce crystallization.

Mass spectrum (FDMS): m/z=169.

$^1$H NMR: d 6.52 (2H), 4.66 (2H), 3.55 (s,3H), 1.92 (2H), 1.38 (1H), 1.25 (1H).

Analysis calculated for $C_8H_{11}NO_3$: C, 56.80; H, 6.55; N, 8.28. Found: C, 56.66; H, 6.54; N, 8.43.

EXAMPLE 48

N-Methoxycarbonyl-3,6-dicarboxy-1-oxa-2-azacyclohexane (VI)

A solution of the compound prepared as described in Example 47 (1.7 g) in toluene (26 ml) was treated with a 0.1M solution of tetrabutylammonium hydrogen sulfate (0.23 g) in water (7 ml). This biphasic mixture was cooled to about −10° C. (ice/acetate bath), and treated with a 0.2M potassium permanganate solution (2.76 g of $KMnO_4$ in 90 ml of water). The permanganate solution was added over a period of about one hour and 20 minutes. The resulting slurry was mechanically stirred for two hours. The reaction mixture was filtered, and the insoluble material washed with ethyl acetate and water. The pH of the filtrate was adjusted from about pH 8.24 to about pH 2.01 by the addition of 1N hydrochloric acid. The phases were separated and the aqueous phase extracted with ethyl acetate (2×25 ml). The combined organics were dried over sodium chloride and magnesium sulfate, filtered, and concentrated in vacuo to give 245 mg of a white powder.

Mass spectrum (FDMS): m/z=234 (M+1), 203 (M+1—$OCH_3$), 144 (M+1—$2CO_2$).

$^1$H NMR: d 4.72 (1H), 4.27 (dd, 1H), 3.64 (s, 3H), 2.16 (1H), 1.85 (2H), 1.52 (1H).

EXAMPLE 49

Methyl 3-(1,2,4-Triazole-1-yl)-2-pyrrolidone-5-carboxylate (IX)

A mixture of the compound prepared as described in Example 4 (318 mg), triphenylphosphine (577 mg), and 1,2,4-triazole (152 mg) in dry tetrahydrofuran (4.5 ml) was cooled to about 5° C., and treated with diethyl azodicarboxylate (383 mg) over a ten minute period. After the addition was complete, the reaction was allowed to warm to room temperature. After about 17 hours, the reaction solution was concentrated in vacuo and allowed to stand at room temperature under reduced pressure to give a crystalline solid. This solid was diluted with chloroform and purified by centrifugal thin-layer chromatography, eluting with ethyl acetate/hexane (1:1) followed by ethyl acetate/hexane (3:1), ethyl acetate, ethyl acetate/methanol (19:1), and ethyl acetate/methanol (9:1). The fractions containing the title compound were combined and concentrated in vacuo to give 280 mg.

Mass spectrum (FABMS): m/z=211 (M+1).

$^1$H NMR: d 8.72 (1H), 8.56 (1H), 7.96 (1H), 5.27 (1H), 4.35 (1H), 2.90 (m, 1H), 2.43 (1H).

Analysis calculated for $C_8H_{10}N_4O_3$: C, 45.72; H, 4.80; N, 26.66. Found: C, 46.02; H, 4.71; N, 26.94.

EXAMPLE 50

4-(1,2,4-Triazol-1-yl)glutamic Acid (41)

The compound prepared as described in Example 49 (420 mg) was treated with 5N hydrochloric acid (10 ml), and the resulting mixture heated to reflux. After 32 hours, the mixture was evaporated to dryness. The residue was diluted with acetone (20 ml), sonicated in an ultrasound bath, and filtered. The solid material was dried in vacuo at room temperature for about 18 hours. This material was dissolved in water (3 ml) and THF (0.2 ml), and purified by cation-exchange chromatography (AG50W-X8), eluting with water followed by tetrahydrofuran/water (1:1) and 10% pyridine. The fractions containing the title compound were combined and evaporated to dryness. The residue was diluted with water (100 ml), and once again evaporated to dryness. This procedure was repeated three more times. The residue was dried at reduced pressure for four days to give a white glass. The glass was treated with acetone, and the resulting mixture filtered. The solid material was dried in vacuo to give 405 mg of the title compound.

Mass spectrum (FABMS): m/z=215 (M+1), 197 (M+1—$H_2O$).

$^1$H NMR: d 8.50 and 8.46 (1H), 7.91 and 7.89 (1H), 5.38 and 5.26 (1H), 4.21, 3.68 and 3.23 (1H), 2.90–2.24 (2H).

EXAMPLE 51

Methyl 3-(Tetrazol-1-yl)-2-pyrrolidone-5-carboxylate and Methyl 3-(Tetrazol-2-yl)-2-pyrrolidone-5-carboxylate (IX)

A mixture of the compound prepared as described in Example 4 (318 mg), triphenylphosphine (577 mg), and tetrazole (155 mg) in dry tetrahydrofuran (4.5 ml) was cooled in an ice/water bath, and treated with diethyl azodicarboxylate (383 mg) over a ten minute period. After the addition was complete, the reaction was allowed to warm to room temperature. After about 17½ hours, the reaction solution was concentrated in vacuo to give a greasy crystalline mass. This material was diluted with chloroform (10 ml) and concentrated in vacuo. This procedure was repeated to remove traces of tetrahydrofuran. The residue was dissolved in chloroform (10 ml) and purified by centrifugal thin-layer chromatography, eluting with ethyl acetate/hexane (1:1) followed by ethyl acetate/hexane (9:1), ethyl acetate, ethyl acetate/methanol (9:1), and ethyl acetate/methanol (4:1). The first isomer to elute was the tetrazol-2-yl compound, and the second isomer to elute was the tetrazol-1-yl compound. Fractions containing each of these isomers in pure form were pooled and concentrated in vacuo. The residue was triturated in methylene chloride (3 ml), and the title compounds isolated by filtration to give 46 mg of the tetrazol-2-yl compound and 227 mg of the tetrazol-1-yl compound.

Methyl 3-(Tetrazol-1-yl)-2-pyrrolidone-5-carboxylate

Mass spectrum (FABMS): m/z=212 (M+1).

$^1$H NMR: d 9.51 (s,1H), 8.96 (s,1H), 5.62 (t,1H), 4.34 (t,1H), 3.70 (s,1H), 3.07 and 2.50 (m,2H).

Analysis calculated for $C_7H_9N_5O_3$: C, 39.81; H, 4.30; N, 33.16. Found: C, 40.06; H, 4.25; N, 33.42.

Methyl 3-(Tetrazol-2-yl)-2-pyrrolidone-5-carboxylate

Mass spectrum (FABMS): m/z=212 (M+1).

$^1$H NMR: d 9.02 (s,1H), 9.00 (s,1H), 5.94 (t,1H), 4.39 (t,1H), 3.71 (s,1H), 3.10 and 2.52 (m,2H).

Analysis calculated for $C_7H_9N_5O_2$: C, 39.81; H, 4.30; N, 33.16. Found: C, 40.02; H, 4.32; N, 32.88.

EXAMPLE 52

4-(Tetrazol-2-yl)glutamic Acid (42)

The title compound was prepared substantially as described in Example 50 from methyl 3-(tetrazol-2-yl)-2-pyrrolidone-5-carboxylate (7 mg).

$^1$H NMR: d 8.88 and 8.87 (1H), 6.70 (m, 1H), 3.94 and 3.65 (1H), 2.80–2.64 (m, 1H), 2.48–2.36 (m, 1H).

EXAMPLE 53

4-(Tetrazol-1-yl)glutamic Acid (43)

The title compound was prepared substantially as described in Example 52 from methyl 3-(tetrazol-1-yl)-2-pyrrolidone-5-carboxylate.

$^1$H NMR (d6-DMSO/d-TFA): d 9.50, 9.48, 8.43 (m), 5.48 (m), 4.13 (m), 3.78 (m), 3.17 (m), 2.89–2.65 (m), 2.24 (m).

EXAMPLE 54

(2S,4R)-N-(t-Butoxycarbonyl)-4-(t-butoxycarbonyloxy)-proline methyl ester (XV)

A solution of 4-hydroxy-L-proline methyl ester hydrochloride (1 g), triethylamine (2.5 ml) and N,N-dimethylaminopyridine (134 mg) in methylene chloride (50 ml) was treated with di-tert-butyldicarbonate (2.8 ml). After 18 hours at room temperature, the solvent was evaporated. The residue was dissolved in ether and extracted with 5% hydrochloric acid, saturated sodium bicarbonate solution, and brine. The organic phase was dried over magnesium sulfate and evaporated to dryness. The title compound was purified by flash chromatography, eluting with hexane/ethyl acetate (10:1), to give 1.8 g.

$[a]_D$=−29.7 (c=1,$CHCl_3$).

$^1$H NMR (200 MHz, $CDCl_3$): d 5.15 (m, 1H), 4.40 (m, 1H), 3.74 (s,3H), 3.90–3.50 (m,2H), 2.60–2.10 (m, 2H), 1.53, 1.50, 1.45 and 1.41 (4s, 18H).

EXAMPLE 55

Methyl (3R,5S)-N-(t-Butoxycarbonyl)-3-(t-butoxycarbonyloxy)-2-pyrrolidone-5-carboxylate (XVI)

A mixture of ruthenium(IV) oxide hydrate (60 mg) and 10% aqueous sodium periodate (30 ml) was treated with a solution of the compound prepared as described in Example 54 (1 g) in ethyl acetate (10 ml). The resulting mixture was vigorously stirred at room temperature. After two days, the phases were separated and the aqueous phase extracted with ethyl acetate. The combined organic solutions were treated with isopropyl alcohol to decompose the remaining ruthenium oxidant. The resulting mixture was filtered over Celite. The filtrate was washed with water, dried over magnesium sulfate, and concentrated in vacuo. The residue was purified by silica-gel flash chromatography, eluting with hexane/ethyl acetate (3:1), to give 906 mg of the title compound.

$[a]_D$=+15.1 (c=1, CHCl$_3$).

$^1$H NMR (200 MHz, CDCl$_3$): d 5.31 (dd, 1H), 4.41 (dd, 1H), 3.80 (s, 3H), 2.70–2.25 (m, 2H), 1.50 (s, 9H).

EXAMPLE 56

Methyl (3R,5S)-3-Hydroxy-2-pyrrolidone-5-carboxylate (XVII)

A solution of the compound prepared as described in Example 55 (1.5 g) in methylene chloride (80 ml) was treated with trifluoroacetic acid (3.3 ml). After two hours at room temperature, the solvent was evaporated. The residue was purified by silica-gel flash chromatography, eluting with ethyl acetate, to give 536 g of the title compound as a white solid. Melting point 99°–100° C.

$[a]_D$=+38.0 (c=0.5, MeOH).

$^1$H NMR (200 MHz, D$_2$O): d 4.24 (m, 2H), 3.50 (s,3H), 2.44 (m, 1H), 2.10 (m, 1H).

EXAMPLE 57

Methyl (3R,5S)-3-(4-Methylphenoxy)-2-pyrrolidone-5-carboxylate (XVIII)

A mixture of the compound prepared as described in Example 56 (477 mg), triphenylphosphine (865 mg) and p-cresol (357 mg) in tetrahydrofuran (5 ml) was cooled to 0° C., and treated with diethyl azodicarboxylate (520 μl). After about 18 hours at room temperature, the reaction mixture was evaporated to dryness. The residue was purified by silica-gel flash chromatography, eluting with hexane/ethyl acetate (3:1), to give the title compound contaminated with triphenylphosphine oxide.

$^1$H NMR (200 MHz, CDCl$_3$): d 7.16–6.80 (4H), 6.18 (bs, 1H), 4.83 (t, 1H), 4.24 (t, 1H), 3.80 (s, 3H), 3.10–2.90 (m, 1H), 2.45–2.20 (m, 1H), 2.29 (s,3H).

EXAMPLE 58

(2S,4S)-4-(4-Methylphenoxy)glutamic Acid (44)

A mixture of the compound prepared as described in Example 57 and 6N hydrochloric acid was heated to reflux. After about 18 hours, the reaction mixture was evaporated to dryness. The title compound was purified by cation-exchange chromatography (DOWEX 50X8-100), eluting with 10% pyridine/water. Melting point 177.8° C. (dec).

$[a]_D$=–38.0 (c=1, 10% pyridine/H$_2$O).

$^1$H NMR (200 MHz, CD$_3$OD+KOD): d 7.04–6.83 (d), 4.25 (dd, 1H), 3.48 (dd, 1H), 2.36–2.27 (m, 1H), 2.21 (s,3H), 2.03–1.96 (m, 1H).

EXAMPLE 59

(2S,4S)-4-(2-Naphthyloxy)glutamic Acid (45)

The title compound was prepared substantially as described in Examples 57 and 58, except using 2-napthol. Melting point 176°–177° C. (dec).

$[a]_D$=–14.0 (c=1, 10% pyridine/H$_2$O).

$^1$H NMR (200 MHz, D$_2$O+CD$_3$OD+KOD): d 7.74–7.65 (m,3H), 7.40–7.18 (m, 4H), 4.73 (dd, 1H), 3.54 (dd, 1H), 2.47–2.38 (m, 1H), 2.11–2.04 (m, 1H).

EXAMPLE 60

(2S,4S)-4-(4-Phenylphenoxy)glutamic Acid (46)

The title compound was prepared substantially as described in Examples 57 and 58, except using 4-phenylphenol.

$[a]_D$=–5.8 (c=1, 10% pyridine/H$_2$O).

$^1$H NMR (200 MHz, CD$_3$OD+KOD): d 7.57–6.99 (m,9H), 4.64 (dd, 1H), 3.49 (dd, 1H), 2.5–2.3 (m, 1H), 2.1–1.9 (m, 1H).

EXAMPLE 61

(2S,4S)-4-(2-Dibenzofuranoxy)glutamic Acid (47)

The title compound was prepared substantially as described in Examples 57 and 58, except using 2-hydroxy-dibenzofuran. Melting point 154°–156° C. (dec).

$[a]_D$=–32.0 (c=0.5, 10% pyridine/H$_2$O).

$^1$H NMR (200 MHz, CD$_3$OD+KOD): d 7.94 (d, 1H), 7.54–7.42 (m, 4H), 7.3 (td, 1H), 7.13 (dd, 1H), 4.68 (dd, 1H), 3.56 (dd, 1H), 2.52–2.38 (m, 1H), 2.11–1.95 (m, 1H).

EXAMPLE 62

4-(4-(4-phenylethenyl)phenoxy)glutamic acid (48)

The title compound was prepared substantially as described in Examples 5 and 6, except using trans-4-hydroxy stilbene.

$^1$H NMR: d 7.50(m,4H), 7.32(t,2H), 7.17(m, 1H), 7.04(d, 2H), 6.77(d,2H), 4.79(t,1H), 3.62(m, 1H), 2.19(m,2H)

Analysis calculated for C$_{19}$H$_{19}$NO$_5$: C, 66.85; H, 5.61; N, 4.10; Found: C, 66.63; H, 5.48; N, 3.87.

EXAMPLE 63

4-(4-(2-phenylethyl)phenoxy)glutamic acid (49)

The title compound was prepared substantially as described in Examples 5 and 6, except using 2-phenylethyl phenol.

Mass spectrum (FDMS): m/z 344(m+1)

$^1$H NMR(DMF$_7$): d 6.91–6.84(m,4H), 6.78(m,3H), 6.39(d,2H), 4.54(t,1H), 3.66(t,1H), 2.45–2.38(m,4H), 2.07(t,2H)

Analysis calculated for C$_{19}$H$_{21}$NO$_5$: C, 66.46; H, 6.16; N, 4.08; Found: C, 66.19; H, 6.20; N, 3.97.

EXAMPLE 64

4-(4-(3-phenylpropyl)phenoxy)glutamic acid (50)

(i) A mixture of dibenzoylmethane (100 g) and 5% palladium on carbon (10.0 g) in ethyl acetate (600 ml) and concentrated sulfuric acid (15 ml) was hydrogenated at a hydrogen pressure of 60 psi and at room temperature. After 2 hours, the reaction was allowed to cool to room temperature. Reaction mixture filtered through talc. The filtrate was treated with water (2×250 ml) and phases separated. The organic phase was treated with saturated aqueous sodium bicarbonate (250 ml). The organic phase was dried over sodium chloride then magnesium sulfate, filtered, concentrated vacuo to give 75.34 g of 1,3-diphenylpropane.

(ii) A solution of 1,3-diphenylpropane (75.34 g) and acetic anhydride (39.18 g) in 1,1,2,2-tetrachloroethane (285 ml) was cooled to a temperature of about –35° C. in an acetone/dry ice bath. To the solution was added aluminum chloride. After the addition of the aluminum chloride was complete (ca. 60 min.), the resulting reaction suspension was allowed to warm to room temperature. After approximately 4.6 hours at room temperature, the reaction was cooled to approximately 0° C. in an water/ice bath, then treated with 6N HCl (114 ml) over a one hour period. The reaction was treated with water (380 ml) and the phases separated. The aqueous layer was treated with chloroform (3×200 ml) and the phases were separated. The combined organic phases were washed with water (200 ml), dried over sodium chloride, filtered and concentrated in vacuo to give an oil. The oil was subjected to vacuum distillation. Distillation at 204°–213 ° C., 0.6 mm Mercury gave 39.07 g of 4'-(3-phenylpropyl)acetophenone as an oil.

(iii) A suspension of 4'-(3-phenylpropyl) acetophenone (39.07 g) and m-chloroperbenzoic acid (124.48 g) in methylene chloride (400ml) was refluxed. (Note: the m-chloroperbenzoic acid used in this reaction was a mixture of 1:1 m-chloroperbenzoic acid and m-chlorobenzoic acid. ) After 23.5 hours, the reaction was allowed to cool to room temperature. After 2 hours at room temperature, the reaction mixture was filtered and the insolubles washed with methylene chloride (100 ml). To the filtrate was added water (500 ml). The pH of the biphasic solution was adjusted from 3.34 to 10.44 with 5N NaOH and the phases were separated. The organic phase was treated with 10% aqueous potassium carbonate (3×500 ml) then with brine (2×500 ml). The organic phase was dried over sodium chloride then magnesium sulfate, filtered, concentrated in vacuo to give 43.4 g of 4-(3-phenylpropyl) phenyl acetate.

(iv) To a mixture of 4-(3-phenylpropyl)phenyl acetate in methanol (610 ml) and water (530 ml) was added sodium carbonate (72.37 g). The resulting suspension was refluxed. After 2.7 hours, the reaction mixture was allowed to cool to room temperature. After 15 minutes, the reaction mixture was treated with concentrated HCl (117 ml) over a 15 minute period. The reaction mixture was then concentrated in vacuo. It was then treated with 1N HCl (500 ml). Next, the reaction mixture was treated with diethyl ether (750 ml) and the phases separated. The aqueous phase was treated with diethyl ether (3×500 ml). The combined organic phases were dried over sodium chloride then magnesium sulfate, filtered and concentrated in vacuo to an oil. The oil was dissolved in acetone then treated with 230–400 mesh silica-gel (76 g), and the resulting mixture evaporated to dryness. The desired compound was isolated by flash silica-gel chromatography, eluting with hexane/ethyl acetate/methanol (96.5:2.5:1, 8×250 ml) then hexane/ethyl acetate/methanol (94:5:1, 4×250 ml) followed by hexane/ethyl acetate/methanol (89:10:1). The fractions containing 4-(3-propylphenyl)phenol were combined and concentrated in vacuo to give an oil. Upon standing at room temperature the oil crystallized out.

(v) A mixture of the compound prepared as described in Example 4 (0.5349 g), triphenylphosphine (1.00 g), and 4-(3-propylphenyl) phenol (0.8100 g) in tetrahydrofuran (4.7 ml) was cooled to approximately 1°–2° C., and treated with a solution of diethylazodicarboxylate (0.6645 g) over a two minute period. After the addition was complete, the reaction suspension was allowed to warm to room temperature. After about 28.5 hours, the resulting brown solution was concentrated in vacuo. The residue was diluted with chloroform (2 ml), the insoluble material removed by filtration, and the filtrate concentrated in vacuo to an oil. The oil was dissolved in methylene chloride and purified by preparative centrifugal thin-layer chromatography (4 mm plate, flow rate=8 ml/min), eluting with 50% ethyl acetate/hexane until the first band elutes then solvent switched to 100% ethyl acetate. The fractions containing the desired compound were combined, dried over magnesium sulfate, filtered and concentrated in vacuo to give 0.916 g of methyl 3-(4-(3-phenylpropyl)phenoxy]-2-pyrrolidone-5-carboxylate as a white solid.

(vi) A mixture of lithium hydroxide (0.0464 g) in water (0.5 ml) and tetrahydrofuran (1.7 ml) was treated with the produce of step (v) (0.2283 g), and heated to 60° C. After about 4.75 hours, the reaction mixture was allowed to cool to room temperature. After approximately one hour at room temperature the reaction mixture was treated with 5N HCl (387 ml), resulting in a biphasic solution. The reaction mixture was then concentrated in vacuo to a solid. The solid material was triturated in toluene (10 ml) and water (10 ml). The insolubles were then collected by filtration to afford 145 mg of 3- [4-(3-phenylpropyl)phenoxy]-2-pyrrolidone-5-carboxylic acid.

$^1$H NMR: d 8.43(1H), 7.24(2H), 7.16–7.05(m,5H), 6.86(2H), 4.82 (t, 1H), 4.07 (t, 1H), 2.87 (m, 1H), 2.53 (4H), 1.88–1.75 (m, 3H).

(vii) A mixture of lithium hydroxide (0.0305 g) in water (0.3 ml) and tetrahydrofuran (1.1 ml) was treated with the produce of Step (vi) (0.1442 g), and heated to 60° C. After about 6.0 hours, the reaction mixture was allowed to cool to room temperature. The reaction mixture was then treated with 5N HCl (255 ml). The insolubles were collected by filtration, washed with 1:1 tetrahydrofuran:water (10 ml), then tetrahydrofuran (5 ml) and finally water (5 ml). The title compound was dried in a vacuum oven at 60° C. overnight.

$^1$H NMR(DMFd$_7$): d: 6.91–6.71(m,7H), 6.39(d,2H), 4.54(t,1H),3.65(t,1H), 2.38–2.02(m, 6H), 1.52–1.42(m,2H).

Analysis calculated for $C_{20}H_{23}NO_5$: C, 67.21; H, 6.49; N, 3.92; Found: C, 66.98, H, 6.37; N, 3.78.

EXAMPLE 65

4-(4-(4-phenylbutyl)phenoxy)glutamic acid (51)

(i) A mixture of 1,4-dibenzoylethane (20 g) and 5% palladium on carbon (2.0 g) in ethyl acetate (375 ml), ethanol (375 ml) and concentrated sulfuric acid (5 ml) was hydrogenated at a hydrogen pressure of 60 psi and at 50° C. After 2 hours, the reaction was allowed to cool to room temperature. The reaction was filtered through talc. The filtrate was concentrated in vacuo. The material was treated with water (250 ml) resulting in crystal formation. The mixture was sonicated and the crystals were collected by filtration to give 1,6-diphenylbutane (17.75 g).

Mass spectrum (FDMS): m/z 210.

$^1$H NMR: d 7.24 (4H), 7.13 (6H), 2.56 (4H), 1.55 (4H).

Analysis calculated for $C_{16}H_{18}$: C, 91.37; H, 8.63; Found: C, 91.39; H, 8.61.

A solution of 1,6-diphenylbutane (15.42 g) and acetic anhydride (7.48 g) in 1,1,2,2-tetrachloroethane (54 ml) was cooled to a temperature of about −20° C. in an acetone/dry ice bath. To the solution was added aluminum chloride (19.55 g) at such a rate as to maintain the temperature below −20° C. After the addition of the aluminum chloride was complete (ca. 40 min.), the resulting reaction suspension was allowed to warm to room temperature. After approximately 2.75 hours at room temperature, the reaction mixture was cooled to approximately 0° C. in an water/ice bath, then treated with 6N HCl (22 ml) over a twenty minute period. The reaction mixture was then treated with water (100 ml) and the phases separated. The aqueous layer was treated with chloroform (3×50 ml) and the phases were separated. The combined organic phases were washed with brine (50 ml), filtered and concentrated in vacuo. The material was dissolved in diethyl ether, then treated with 230–400 mesh silica-gel (42 g), and the resulting mixture evaporated to dryness. The material was subjected to flash silica-gel filtration, eluting with hexane/ethyl acetate (4: 1, 10×250 ml). The fractions containing the desired material were concentrated in vacuo to give an oil. Distillation at 197°–210° C., 0.3 mm Mercury gave 7.70 g of 4'-(4-phenylbutane)acetophenone as an oil.

Mass spectrum (FDMS): m/z 252.

$^1$H NMR: d 7.84 (d,2H), 7.31–7.20 (4H), 7.13 (3H), 2.64 (t,2H), 2.56 (t,2H), 2.51 (s, 3H), 1.55 (4H).

(iii) A suspension of 4'-(4-phenylbutyl) acetophenone (7.63 g) and m-chloroperbenzoic acid (22.95 g) in methylene chloride (75 ml) was refluxed. (Note: the m-chloroperbenzoic acid used in this reaction was a mixture of 1:1 m-chloroperbenzoic acid and m-chlorobenzoic acid). After 25.25 hours, the reaction was allowed to cool to room temperature. After approximately 2.3 hours at room temperature, the reaction mixture was filtered and the insolubles washed with methylene chloride (50 ml). To the filtrate was added water (100 ml). The pH of the biphasic solution was adjusted from 2.77 to 10.18 with 5N NaOH (12 ml) and the phases were separated. The organic phase was treated with 10% aqueous potassium carbonate (3×50 ml) then with brine (3×100 ml). The organic phase was dried over sodium chloride then magnesium sulfate, filtered and concentrated in vacuo to give a 8.31 g of 4'-(4-phenylbutyl)phenyl acetate.

Mass spectrum (FDMS): m/z 268.

$^1$H NMR: d 7.26–7.14 (7H), 6.68 (2H), 2.57 (4H), 2.21 (s, 3H), 1.56 (4H).

(iv) To a mixture of 4-(4-phenylbutyl)phenyl acetate (8.29 g) in methanol (112 ml) and water (97 ml) was added sodium carbonate (13.10 g). The reaction was refluxed. After 3.5 hours, the reaction mixture was allowed to cool to room temperature. After 25 minutes at room temperature, the reaction mixture was treated with 5N HCl (50 ml). It was then concentrated in vacuo to remove the majority of the methanol present. Diethyl ether (250 ml) was added to the residue, then the material was treated with 1N HCl (3×100 ml) and the phases were separated. The material was dissolved in diethyl ether, then the denied compound was isolated by flash silica-gel filtration, eluting with hexane/ethyl acetate (20:1, 92×13 ml). The fractions containing the denied compound were combined and concentrated in vacuo to give 1.57 g of 4-(4-phenyl butyl)phenol an oil. Upon standing at room temperature the oil crystallized out.

$^1$H NMR: d 9.06 (s, 1H exchangeable), 7.23 (2H), 7.12 (3H), 6.91 (2H), 6.61 (2H), 2.55 (2H), 2.45 (2H), 1.57–1.45 (4H).

(v) A mixture of the compound prepared as described in Example 4 (0.434 g), triphenylphosphine (0.8113 g), and 4-(4-phenylbutyl)phenol (0.700 g) in tetrahydrofuran (3.8 ml) was cooled to approximately 1°–2° C., and treated with diethylazodicarboxylate (0.5386 g) over a two minute period. After the addition was complete, the reaction was allowed to warm to room temperature. After about 23 hours, the solution was concentrated in vacuo. The residue was diluted with chloroform (1 ml), the insoluble material removed by filtration, and the filtrate concentrated in vacuo. The residual oil was dissolved in methylene chloride (4 ml) and purified by preparative centrifugal thin-layer chromatography (4 mm plate, flow rate=8 ml/min), eluting with 50% ethyl acetate/hexane until first band elutes then solvent switched to 100% ethyl acetate. The fractions containing the desired compound were combined, dried over magnesium sulfate, filtered and concentrated in vacuo to give methyl 3-[4-(4-phenylbutyl)phenoxy]-2-pyrrolidone-5-carboxylate (583 mg).

$^1$H NMR: d 7.23 (2H), 7.13 (3H), 7.04 (2H), 6.85 (d, 2H), 4.83 (t, 1H), 4.21 (t, 1H), 3.65 (s, 3H), 2.93–2.83 (m, 1H), 2.54 (m, 4H), 1.89 (m, 1H), 1.53 (4H).

(vi) A mixture of lithium hydroxide (0.072 g) in water (0.9 ml) and tetrahydrofuran (2.9 ml) was treated with methyl 3-[4-(4-phenylbutyl) phenoxy]-2-pyrrolidone-5-carboxylate (0.370 g), and heated to 60° C. After about 4.0 hours, the reaction mixture was allowed to cool to room temperature. After approximately 2.25 hours at room temperature, the reaction mixture was treated with 5N HCl (604 ml). The resulting biphasic solution was cooled to 5° C. for approximately 18 hours. The biphasic solution was treated with water (2 ml). The resulting milky solution was sonicated resulting in crystal formation. The crystals were collected by filtration, washed with 1:1 THF:water (10 ml), THF (10 ml), and water (10 ml). The crystals were then dried overnight in at vacuum oven at 60° C. to afford the title compound (106 mg).

Mass spectrum (FABMS): m/z 372 (m+1).

$^1$H NMR: d 7.23(m,2H), 7.13(m,3H), 7.03(d,2H), 6.66(d, 2H), 4.71(1H), 3.62(1H), 2.57–2.51(m, 3H),2.26–2.06 (m, 3H), 1.56–1.50 (m, 4H).

Analysis calculated for $C_{21}H_{25}NO_5$: C, 67.91; H, 6.78; N, 3.77; Found: C, 68.20; H, 6.93; N, 3.85.

We claim:

1. A method of affecting one or more excitatory amino acid receptors in mammals, which comprises administering to a mammal requiring modulated excitatory amino acid neurotransmission a pharmaceutically-effective amount of a compound of the formula

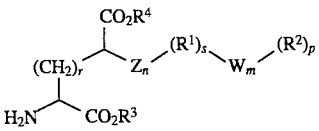

wherein:

Z is $NR^5$, O, or S;

W is $CH_{(3-p)}$, $-(CH_2)_q-$, $-(CH_2)_qCH_{(3-p)}$, $-(CH_2)_qCO-$, $-(CH_2)_qO-$, $-(CH_2)_qCH=CH(CH_2)_q-$, $-(CH_2)_qCH=CH-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

n is 0 or 1; m is 0 or 1; p is 0, 1, 2, or 3; q is 0–6; r is or 2; s is 0 or 1, provided that the sum of n, m, p and s is at least 1;

$R^1$ and $R^2$ are independently aryl, substituted aryl, heterocycle, or substituted heterocycle;

$R^3$ is hydrogen or a carboxy protecting group;

$R^4$ is hydrogen or a carboxy protecting group;

$R^5$ is hydrogen, $C_1$–$C_{10}$ alkyl, acyl, or $SO_2(C_1$–$C_4$ alkyl);

$R^6$ is $C_1$–$C_{10}$ alkyl;

provided that when n is 0 and s is 1, $R^1$ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl;

further provided that when n is 1, m is 1, and W is $NR^5$, O, S, SO, or $SO_2$, s is 1; and when n is 0 and s is 0, m is 1 and W is $-(CH_2)_qCO-$, $-(CH_2)_qO-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

or a pharmaceutically acceptable salt thereof.

2. A method of claim 1, wherein:

Z is $NR^5$, O or S;

W is $CH_{(3-p)}$, —$(CH_2)_q$—, —$(CH_2)_qCH_{(3-p)}$, —$(CH_2)_qCO$—, —$(CH_2)_qCH=CH(CH_2)_q$—, —$(CH_2)_qCH=CH$—; —CH=CHCO—, —CH=CHCOR⁶, —$(CH_2)_q$CHCOR⁶, —$(CH_2)_q$COR⁶, —$O(CH_2)_q$—, NR⁵, O, S, SO or $SO_2$;

n is 0 or 1; m is 0 or 1; p is 0, 1, 2 or 3; q is 0-6; r is 1 or 2; s is 0 or 1;

R¹ and R² are independently aryl, substituted aryl, heterocycle, or substituted heterocycle;

R³ is hydrogen or a carboxy protecting group;

R⁴ is hydrogen or a carboxy protecting group;

R⁵ is hydrogen, $C_1$–$C_{10}$ alkyl, aryl, or $SO_2$ ($C_1$–$C_4$ alkyl);

R⁶ is $C_1$–$C_{10}$ alkyl;

provided that when n is 0, s is 1 and R¹ is selected from the group consisting of tetrazolyl, triazolyl, pyridazinyl, pyrimidinyl, pteridinyl, 1,2,4-triazine-3,5-dionyl, pyrazolonyl, H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl;

further provided that when n is 1, m is 1, and W is —$O(CH_2)_q$—NR⁵, O, S, SO, or $SO_2$, s is 1;

or a pharmaceutically acceptable salt thereof.

3. A method of claim 2 wherein:

Z is O or S

W is —$(CH_2)_qCH=CH$—, —$(CH_2)_q$—, —$(CH_2)_qO$—, —$(CH_2)_qCH=CH(CH_2)_q$—, —$O(CH_2)_q$—;

n is 1, s is 1, p is 0 or 1, and q is 0–6.

4. A method of claim 3 wherein:

R¹ is aryl or substituted aryl;

R² is phenyl or substituted phenyl;

R³ and R⁴ are hydrogen;

Z is O; and q is 1–6;

r is 1.

5. A method as claimed in claim 1, in which;

Z is O or S;

W is —$(CH_2)_qCH=CH$—, —$(CH_2)_q$—, —$(CH_2)_qO$—, —$(CH_2)_qCH=CH(CH_2)_q$—, —$O(CH_2)_q$—; and (i) n is 0, s is 1, m is 0, p is 0 and R¹ is tetrazolyl or triazolyl;

(ii) n is 1, s is 1, m is 0, p is 0 and R¹ is phenyl or naphthyl which is unsubstituted or substituted by one or two substituents chosen from the group consisting of halogen, hydroxy, cyano, nitro, $C_1$–$C_6$ alkyl, $C_7$–$C_{10}$ alkyl, $C_3$–$C_6$ cycloalkyl, $C_1$–$C_4$ alkoxy, carboxy, acetyl, formyl, carboxymethyl, hydroxymethyl, amino, aminomethyl and trifluoromethyl, or is disubstituted on two adjacent carbon atoms by a $C_3$–$C_{10}$ alkylene, $C_2$–$C_{10}$ alkylenoxy, $C_1$–$C_{10}$ alkylenedioxy, $C_5$–$C_6$ cycloalkylene or $C_5$–$C_6$ cycloalkyleneoxy group which, together with the two adjacent carbon atoms in the aryl ring to which it is attached forms a ring; or pyrimidyl or 1-methyltetrazol-5-yl; or (iii) n is 1, s is 1, m is 0 or 1, p is 1 or 2, R¹ is phenyl or triazolyl and each R² is selected independently from pyridyl and phenyl which is unsubstituted or substituted by one or two substituents chosen from the group consisting of halogen, hydroxy, cyano, nitro, $C_1$–$C_6$ alkyl, $C_7$–$C_{10}$ alkyl, $C_3$–$C_6$ cycloalkyl, $C_1$–$C_4$ alkoxy, carboxy, acetyl, formyl, carboxymethyl, hydroxymethyl, amino, aminomethyl and trifluoromethyl; and r is 1; and R³ and R⁴ are each hydrogen.

6. A method as claimed in claim 1, in which

Z is O or S;

W is —CH=CH—, —$(CH_2)CH=CH$,—, —$CH_2$—, —$(CH_2)_3$—, —$(CH_2)_4$—, —$(CH_2)_6$—, O or —$CH_2O$—; and (i) n is 0, s is 1, m is 0, p is 0 and R¹ is tetrazol-1-yl, tetrazol-2-yl or 1,2,4-triazol-2-yl;

(ii) n is 1, s is 1, m is 0, p is 0 and R¹ is phenyl, 2-methylphenyl, 4-methylphenyl, 4-methoxyphenyl, 4-isopropylphenyl, 4-cyclopentylphenyl, 4-(1,1,4,4-tetramethylbutyl)phenyl, 4-acetylphenyl, 4-trifluoromethylphenyl, 4-chlorophenyl, 2-bromophenyl, 3-iodophenyl, 1-naphthyl, 2-naphthyl, 6-bromonaphth-2-yl, 1,6-dibromonaphth-2-yl, 3,4-methylenedioxyphenyl, indan-5-yl, 1,2,3,4-tetrahydronaphthyl, 1,1,4,4-tetramethyl-1,2,3,4-tetrahydronaphthyl, fluoren-2-yl, dibenzofuran-2-yl, 5,6,7,8-tetrahydrodibenzofuran-2-yl, 2-methylbenzofuran-5-yl, benzothiophen-5-yl, pyrimidin-2-yl or 1-methyltetrazol-5-yl; or (iii) n is 1, s is 1, m is 0 or 1, p is 1 or 2, R¹ is phenyl or 1,2,4-triazol-2-yl and each R² is selected independently from 2-pyridyl, phenyl, 2-chlorophenyl, 4-chlorophenyl, and 4-nitrophenyl;

r is 1; and

R³ and R⁴ are each hydrogen.

7. A method as claimed in any one of claims 1 to 6, in which the compound of formula I is in the 2S,4S or 2S,5S configuration.

8. A method of claim 1 in which the compound of formula I is selected from the group consisting of 4-(4-methylphenoxy)glutamic acid, 4-4-(6-phenylhexyl)phenoxy)glutamic acid, 4-(4-(3-phenylprop-2 -eneyl)phenoxy)glutamic acid, 4-(2-naphthyloxy)glutamic acid, 4-(6-bromo-2-naphthyloxy)glutamic acid, 4-(4-(2-(4-nitrophenyl) ethenyl)phenoxy)glutamic acid, 4-(2fluorenoxy)glutamic acid, 4-(2-dibenzofuranoxy)glutamic acid, and 4-(5,6,7,8-tetrahydro-2-dibenzofuranoxy)glutamic acid.

9. The method of claim 8 in which the compound of formula I is 4-(4-(6-phenylhexyl)phenoxy)glutamic acid.

10. The method of claim 8 in which the compound of formula I is (2S,4S)-4-(4-(6-phenylhexyl) phenoxy) glutamic acid.

11. The method of claim 8 in which the compound of formula I is 4-(6-bromo-2-naphthyloxy)glutamic acid.

12. The method of claim 8 in which the compound of formula I is (2S,4S)-4-(6-bromo-2-naphthyloxy)glutamic acid.

13. A method of affecting the metabotropic excitatory amino acid receptor in mammals, which comprises administering to a mammal requiring modulated excitatory amino acid neurotransmission a pharmaceutically-effective amount of a compound of the formula

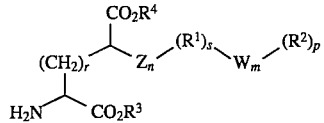

wherein:

Z is NR⁵, O, or S;

W is $CH_{(3-p)}$, —$(CH_2)_q$—, —$(CH_2)_qCH_{(3-p)}$, —$(CH_2)_qCO$—, —$(CH_2)_qO$—, —$(CH_2)_qCH=CH(CH_2)_q$—, —$(CH_2)_qCH=CH$—, —CH=CHCO—, —CH=CHCOR⁶,

—$(CH_2)_qCHOHR^6$, —$(CH_2)_qCHOH$—, —$(CH_2)_qCOR^6$, —$O(CH_2)_q$—, $NR^5$, O, S, SO, or $SO_2$;

n is 0 or 1; m is 0 or 1; p is 0, 1, 2, or 3; q is 0–6; r is 1 or 2; s is 0 or 1, provided that the sum of n, m, p and s is at least 1;

$R^1$ and $R^2$ are independently aryl, substituted aryl, heterocycle, or substituted heterocycle;

$R^3$ is hydrogen or a carboxy protecting group;

$R^4$ is hydrogen or a carboxy protecting group;

$R^5$ is hydrogen, $C_1$–$C_{10}$ alkyl, acyl, or $SO_2$ ($C_1$–$C_4$ alkyl);

$R^6$ is $C_1$–$C_{10}$ alkyl;

provided that when n is 0 and s is 1, $R^1$ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl;

further provided that when n is 1, m is 1, and W is $NR^5$, O, S, SO, or $SO_2$, s is 1; and when n is 0 and s is 0, m is 1 and W is —$(CH_2)_qCO$—, —$(CH_2)_qO$—, —CH=CHCO—, —CH=CHCOR$^6$, —$(CH_2)_qCHOHR^6$, —$(CH_2)_qCHOH$—, —$(CH_2)_qCOR^6$, —$O(CH_2)_q$—, $NR^5$, O, S, SO, or $SO_2$;

or a pharmaceutically acceptable salt thereof.

14. A method of claim 13, wherein:

Z is $NR^5$, O or S;

W is $CH_{(3-p)}$, —$(CH_2)_q$—, —$(CH_2)_qCH_{(3-p)}$, —$(CH_2)_qCO$—, —$(CH_2)_qCH=CH(CH_2)_q$—, —$(CH_2)_qCH=CH$—; —CH=CHCO—, —CH=CHCOR$^6$, —$(CH_2)_qCHCOR^6$, —$(CH_2)_qCOR^6$, —$O(CH_2)_q$—, $NR^5$, O, S, SO or $SO_2$;

n is 0 or 1; m is 0 or 1; p is 0, 1, 2 or 3; q is 0–6; r is 1 or 2; s is 0 or 1;

$R^1$ and $R^2$ are independently aryl, substituted aryl, heterocycle, or substituted heterocycle;

$R^3$ is hydrogen or a carboxy protecting group;

$R^4$ is hydrogen or a carboxy protecting group;

$R^5$ is hydrogen, $C_1$–$C_{10}$ alkyl, aryl, or $SO_2$ ($C_1$–$C_4$ alkyl);

$R^6$ is $C_1$–$C_{10}$ alkyl;

provided that when n is 0, s is 1 and $R^1$ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl;

further provided that when n is 1, m is 1, and W is —$O(CH_2)_q$—, $NR^5$, O, S, SO, or $SO_2$, s is 1;

or a pharmaceutically acceptable salt thereof.

15. A method of claim 11 wherein:

Z is O or S

W is —$(CH_2)_qCH=CH$—, —$(CH_2)_q$—, —$(CH_2)_qO$—, —$(CH_2)_qCH=CH(CH_2)_q$—, —$O(CH_2)_q$—;

n is 1, s is 1, p is 0 or 1, and q is 0–6.

16. A method of claim 15 wherein:

$R^1$ is aryl or substituted aryl;

$R^2$ is phenyl or substituted phenyl;

$R^3$ and $R^4$ are hydrogen;

Z is 0; and q is 1–6;

r is 1.

17. A method as claimed in claim 13, in which;

Z is O or S;

W is —$(CH_2)_qCH=CH$—, —$(CH_2)_q$—, —$(CH_2)_qO$—, —$(CH_2)_qCH=CH(CH_2)_q$—, —$O(CH_2)_q$—; and (i) n is 0, s is 1, m is 0, p is 0 and $R^1$ is tetrazolyl or triazolyl;

(ii) n is 1, s is 1, m is 0, p is 0 and $R^1$ is phenyl or naphthyl which is unsubstituted or substituted by one or two substituents chosen from the group consisting of halogen, hydroxy, cyano, nitro, $C_1$–$C_6$ alkyl, $C_7$–$C_{10}$ alkyl, $C_3$–$C_6$ cycloalkyl, $C_1$–$C_4$ alkoxy, carboxy, acetyl, formyl, carboxymethyl, hydroxymethyl, amino, aminomethyl and trifluoromethyl, or is disubstituted on two adjacent carbon atoms by a $C_3$–$C_{10}$ alkylene, $C_2$–$C_{10}$ alkylenoxy, $C_1$–$C_{10}$ alkylenedioxy, $C_5$–$C_6$ cycloalkylene or $C_5$–$C_6$ cycloalkyleneoxy group which, together with the two adjacent carbon atoms in the aryl ring to which it is attached forms a ring; or pyrimidyl or 1-methyltetrazol-5-yl; or (iii) n is 1, s is 1, m is 0 or 1, p is 1 or 2, $R^1$ is phenyl or triazolyl and each $R^2$ is selected independently from pyridyl and phenyl which is unsubstituted or substituted by one or two substituents chosen from the group consisting of halogen, hydroxy, cyano, nitro, $C_1$–$C_6$ alkyl, $C_7$–$C_{10}$ alkyl, $C_3$–$C_6$ cycloalkyl, $C_1$–$C_4$ alkoxy, carboxy, acetyl, formyl, carboxymethyl, hydroxymethyl, amino, aminomethyl and trifluoromethyl; and r is 1; and $R^3$ and $R^4$ are each hydrogen.

18. A method as claimed in claim 13, in which

Z is O or S;

W is —CH=CH—, —$(CH_2)$CH=CH,—, —$CH_2$—, —$(CH_2)_3$—, —$(CH_2)_4$—, —$(CH_2)_6$—, O or —$CH_2O$—; and (i) n is 0, s is 1, m is 0, p is 0 and $R^1$ is tetrazol-1-yl, tetrazol-2-yl or 1,2,4-triazol-2-yl;

(ii) n is 1, s is 1, m is 0, p is 0 and $R^1$ is phenyl, 2-methylphenyl, 4-methylphenyl, 4-methoxyphenyl, 4-isopropylphenyl, 4-cyclopentylphenyl, 4-(1,1,4,4-tetramethylbutyl)phenyl, 4-acetylphenyl, 4-trifluoromethylphenyl, 4-chlorophenyl, 2-bromophenyl, 3-iodophenyl, 1-naphthyl, 2-naphthyl, 6-bromonaphth-2-yl, 1,6-dibromonaphth-2-yl, 3,4-methylenedioxyphenyl, indan-5-yl, 1,2,3,4-tetrahydronaphthyl, 1,1,4,4-tetramethyl-1,2,3,4-tetrahydronaphthyl, fluoren-2-yl, dibenzofuran-2-yl, 5,6,7,8-tetrahydrodibenzofuran-2-yl, 2-methylbenzofuran-5-yl, benzothiophen-5-yl, pyrimidin-2-yl or 1-methyltetrazol-5-yl; or (iii) n is 1, s is 1, m is 0 or 1, p is 1 or 2, $R^1$ is phenyl or 1,2,4-triazol-2-yl and each $R^2$ is selected independently from 2-pyridyl, phenyl, 2-chlorophenyl, 4-chlorophenyl, and 4-nitrophenyl;

r is 1; and $R^3$ and $R^4$ are each hydrogen.

19. A method as claimed in any one of claims 13 to 18, in which the compound of formula I is in the 2S,4S or 2S,5S configuration.

20. A method of claim 13 in which the compound of formula I is selected from the group consisting of 4-(4-methylphenoxy)glutamic acid, 4-(4-(6-phenylhexyl)phenoxy)glutamic acid, 4-(4-(3-phenylprop-2-enyl)phenoxy)glutamic acid, 4-(2-naphthyloxy)glutamic acid, 4-(6-bromo-2-naphthyloxy)glutamic acid, 4-(4-(2-(4-nitrophenyl)ethenyl)phenoxy)glutamic acid, 4-(2- fluorenoxy)glutamic acid, 4-(2-dibenzofuranoxy)glutamic acid, and 4-(5,6,7,8-tetrahydro-2-dibenzofuranoxy)glutamic acid.

21. The method of claim 20 in which the compound of formula I is 4-(4-(6-phenylhexyl)phenoxy)glutamic acid.

22. The method of claim 20 in which the compound of formula I is (2S,4S)-4-(4-(6-phenylhexyl)phenoxy)glutamic acid.

23. The method of claim 20 in which the compound of formula I is 4-(6-bromo-2-naphthyloxy)glutamic acid.

24. The method of claim 20 in which the compound of formula I is (2S,4S)-4-(6-bromo-2-naphthyloxy)glutamic acid.

25. A method of affecting the NMDA excitatory amino acid receptor in mammals, which comprises administering to a mammal requiring modulated excitatory amino acid neurotransmission a pharmaceutically-effective amount of a compound of the formula

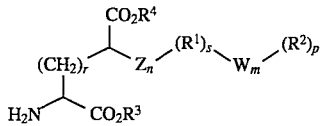   I wherein:

Z is $NR^5$, O, or S;

W is $CH_{(3-p)}$, $-(CH_2)_q-$, $-(CH_2)_qCH_{(3-p)}$, $-(CH_2)_qCO-$, $-(CH_2)_qO-$, $-(CH_2)_qCH=CH(CH_2)_q-$, $-(CH_2)_qCH=CH-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

n is 0 or 1; m is 0 or 1; p is 0, 1, 2, or 3; q is 0–6; r is 1 or 2; s is 0 or 1, provided that the sum of n, m, p and s is at least 1;

$R^1$ and $R^2$ are independently aryl, substituted aryl, heterocycle, or substituted heterocycle;

$R^3$ is hydrogen or a carboxy protecting group;

$R^4$ is hydrogen or a carboxy protecting group;

$R^5$ is hydrogen, $C_1$–$C_{10}$ alkyl, acyl, or $SO_2(C_1$–$C_4$ alkyl);

$R^6$ is $C_1$–$C_{10}$ alkyl;

provided that when n is 0 and s is 1, $R^1$ is selected from the group consisting of tetrazolyl, triazolyl, pyridazinyl, pyrimidinyl, pteridinyl, 1,2,4-triazine-3,5-dionyl, pyrazolonyl, 7H-purinyl, xanthinyl, 3-ethyl-5-hydroxy-1,2,4-thiadiazolyl, 3-hydroxy-1,2,4-thiadiazolyl, rhodaninyl, hydantoinyl, and pseudothiohydantoinyl;

further provided that when n is 1, m is 1, and W is $NR^5$, O, S, SO, or $SO_2$, s is 1; and when n is 0 and s is 0, m is 1 and W is $-(CH_2)_qCO-$, $-(CH_2)_qO-$, $-CH=CHCO-$, $-CH=CHCOR^6$, $-(CH_2)_qCHOHR^6$, $-(CH_2)_qCHOH-$, $-(CH_2)_qCOR^6$, $-O(CH_2)_q-$, $NR^5$, O, S, SO, or $SO_2$;

or a pharmaceutically acceptable salt thereof.

26. A method of claim 25 in which the compound of formula I is selected from the group consisting of 4-(4-methylphenoxy)glutamic acid, 4-(4-(6-phenylhexyl)phenoxy)glutamic acid, 4-(4-(3-phenylprop-2-eneyl)phenoxy) glutamic acid, 4-(2-naphthyloxy)glutamic acid, 4-(6-bromo-2-naphthyloxy)glutamic acid, 4-(4-(2-(4-nitrophenyl) ethenyl)phenoxy)glutamic acid, 4-(2-fluorenoxy) glutamic acid, 4-(2-dibenzofuranoxy)glutamic acid, and 4-(5,6,7,8-tetrahydro-2-dibenzofuranoxy)glutamic acid.

* * * * *

UNITED STATES PATENT AND TRADEMARK OFFICE
CERTIFICATE OF CORRECTION

PATENT NO. : 5,576,323

DATED : November 19, 1996

INVENTOR(S) : Heinz, et al.

It is certified that error appears in the above-identified patent and that said Letters Patent is hereby corrected as shown below:

Column 19, Line 65, "rosylate" should read --tosylate--;

Column 32, Line 23, "3x1600 ml) should read --(3x1600 ml)--;

Column 32, Line 29, "lilt rate" should read --filtrate--;

Column 33, Line 4, "ml" should read --ml--.

Column 36, Line 23, "(M-$H_2O$)(M+1-$CO_2$)" should read --(M-$H_2O$)164(M+1-$CO_2$)--;

Column 43, Line 48, "Example (0.800" should read --Example 4 (0.800)--;

Column 44, Line 14, "insolubles were dried overnight in at vacuum" should read -- insolubles were dried overnight in a vacuum--;

Column 45, Line 5, "(M+1-$H_2O$)(M+1-$CO_2$)" should read --(M+1-$H_2O$)39(M+1-$CO_2$);

Column 55, Line 19, The change requested in column 55, line 19 has been modified by adding after Pyrazolonyl, and before H the number – 7 --.

Signed and Sealed this

Fourth Day of July, 2000

Attest:

*Attesting Officer*

Q. TODD DICKINSON

*Director of Patents and Trademarks*